US012682983B2

(12) United States Patent
Umbarger et al.

(10) Patent No.: US 12,682,983 B2
(45) Date of Patent: Jul. 14, 2026

(54) METHODS OF QUALITY CONTROL USING SINGLE-NUCLEOTIDE POLYMORPHISMS IN PRE-IMPLANTATION GENETIC SCREENING

(71) Applicant: Laboratory Corporation of America Holdings, Burlington, NC (US)

(72) Inventors: Mark Umbarger, Brookline, MA (US); Athurva Gore, Cambridge, MA (US); Gregory Porreca, Cambridge, MA (US)

(73) Assignee: Laboratory Corporation of America Holdings, Burlington, NC (US)

( * ) Notice: Subject to any disclaimer, the term of this patent is extended or adjusted under 35 U.S.C. 154(b) by 1592 days.

(21) Appl. No.: 16/985,980

(22) Filed: Aug. 5, 2020

(65) Prior Publication Data

US 2021/0090687 A1    Mar. 25, 2021

Related U.S. Application Data

(63) Continuation of application No. 14/995,354, filed on Jan. 14, 2016, now abandoned.

(60) Provisional application No. 62/103,802, filed on Jan. 15, 2015.

(51) Int. Cl.
| | |
|---|---|
| *G16B 30/00* | (2019.01) |
| *C12Q 1/6809* | (2018.01) |
| *C12Q 1/6827* | (2018.01) |
| *C12Q 1/6881* | (2018.01) |
| *C12Q 1/6883* | (2018.01) |

(52) U.S. Cl.
CPC ........... *G16B 30/00* (2019.02); *C12Q 1/6809* (2013.01); *C12Q 1/6827* (2013.01); *C12Q 1/6881* (2013.01); *C12Q 1/6883* (2013.01); *C12Q 2600/106* (2013.01); *C12Q 2600/156* (2013.01); *C12Q 2600/172* (2013.01)

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. |
| 4,683,202 A | 7/1987 | Mullis |
| 4,988,617 A | 1/1991 | Landegren et al. |
| 5,060,980 A | 10/1991 | Johnson et al. |
| 5,210,015 A | 5/1993 | Gelfand et al. |
| 5,234,809 A | 8/1993 | Boom et al. |
| 5,242,794 A | 9/1993 | Whiteley et al. |
| 5,348,853 A | 9/1994 | Wang et al. |
| 5,459,307 A | 10/1995 | Klotz, Jr. |
| 5,486,686 A | 1/1996 | Zdybel, Jr. et al. |
| 5,494,810 A | 2/1996 | Barany et al. |
| 5,567,583 A | 10/1996 | Wang et al. |
| 5,583,024 A | 12/1996 | McElroy et al. |
| 5,604,097 A | 2/1997 | Brenner |
| 5,635,400 A | 6/1997 | Brenner |
| 5,674,713 A | 10/1997 | McElroy et al. |
| 5,695,934 A | 12/1997 | Brenner |
| 5,700,673 A | 12/1997 | McElroy et al. |
| 5,701,256 A | 12/1997 | Marr et al. |
| 5,830,064 A | 11/1998 | Bradish et al. |
| 5,846,719 A | 12/1998 | Brenner et al. |
| 5,863,722 A | 1/1999 | Brenner |
| 5,866,337 A | 2/1999 | Schon |
| 5,869,252 A | 2/1999 | Bouma et al. |
| 5,869,717 A | 2/1999 | Frame et al. |
| 5,871,921 A | 2/1999 | Landegren et al. |
| 5,888,788 A | 3/1999 | De Miniac |
| 5,942,391 A | 8/1999 | Zhang et al. |
| 5,993,611 A | 11/1999 | Moroney, III et al. |
| 5,994,056 A | 11/1999 | Higuchi |
| 6,033,854 A | 3/2000 | Kumit et al. |
| 6,033,872 A | 3/2000 | Bergsma et al. |
| 6,100,099 A | 8/2000 | Gordon et al. |
| 6,138,077 A | 10/2000 | Brenner |
| 6,150,516 A | 11/2000 | Brenner et al. |
| 6,171,785 B1 | 1/2001 | Higuchi |
| 6,172,214 B1 | 1/2001 | Brenner |
| 6,172,218 B1 | 1/2001 | Brenner |

(Continued)

FOREIGN PATENT DOCUMENTS

| | | |
|---|---|---|
| EP | 1 321 477 A1 | 6/2003 |
| EP | 1 564 306 A2 | 8/2005 |

(Continued)

OTHER PUBLICATIONS

Kinde et al FAST-SeqS: A Simple and Efficient Method for the Detection of Aneuploidy by Massively Parallel Sequencing PLoS ONE |Jul. 1, 2012 | vol. 7 | Issue 7 | e41162.*

(Continued)

*Primary Examiner* — Joseph Woitach

(74) *Attorney, Agent, or Firm* — Wolf, Greenfield & Sacks, P.C.

(57) ABSTRACT

The present invention provides methods for validating results of a pre-implantation genetic screen. Methods of the invention increase the efficacy of the common PGS assay FAST-SeqS by taking advantage of single-nucleotide polymorphisms (SNPs) generated from the assay to confirm copy number calls, detect errors, identify samples, and recognize and identify sources of contamination. Methods of the invention increase the reliability of a PGS result, thereby making embryo selection more precise and improving outcomes of in vitro fertilization.

19 Claims, 3 Drawing Sheets

(56)        References Cited

U.S. PATENT DOCUMENTS

| | | | |
|---|---|---|---|
| 6,197,508 | B1 | 3/2001 | Stanley |
| 6,197,574 | B1 | 3/2001 | Miyamoto et al. |
| 6,210,891 | B1 | 4/2001 | Nyren et al. |
| 6,223,128 | B1 | 4/2001 | Allex et al. |
| 6,235,472 | B1 | 5/2001 | Landegren et al. |
| 6,235,475 | B1 | 5/2001 | Brenner et al. |
| 6,235,501 | B1 | 5/2001 | Gautsch et al. |
| 6,235,502 | B1 | 5/2001 | Weissman et al. |
| 6,258,568 | B1 | 7/2001 | Nyren |
| 6,274,320 | B1 | 8/2001 | Rothberg et al. |
| 6,306,597 | B1 | 10/2001 | Macevicz |
| 6,352,828 | B1 | 3/2002 | Brenner |
| 6,360,235 | B1 | 3/2002 | Tilt et al. |
| 6,361,940 | B1 | 3/2002 | Van Ness et al. |
| 6,403,320 | B1 | 6/2002 | Read et al. |
| 6,462,254 | B1 | 10/2002 | Vernachio et al. |
| 6,489,105 | B1 | 12/2002 | Matlashewski et al. |
| 6,558,928 | B1 | 5/2003 | Landegren |
| 6,569,920 | B1 | 5/2003 | Wen et al. |
| 6,582,938 | B1 | 6/2003 | Su et al. |
| 6,585,938 | B1 | 7/2003 | Machida et al. |
| 6,613,516 | B1 | 9/2003 | Christians et al. |
| 6,714,874 | B1 | 3/2004 | Myers et al. |
| 6,716,580 | B2 | 4/2004 | Gold et al. |
| 6,719,449 | B1 | 4/2004 | Laugham, Jr. et al. |
| 6,818,395 | B1 | 11/2004 | Quake et al. |
| 6,828,100 | B1 | 12/2004 | Ronaghi |
| 6,833,246 | B2 | 12/2004 | Balasubramanian |
| 6,858,412 | B2 | 2/2005 | Willis et al. |
| 6,911,345 | B2 | 6/2005 | Quake et al. |
| 6,913,879 | B1 | 7/2005 | Schena |
| 6,927,024 | B2 | 8/2005 | Dodge et al. |
| 6,941,317 | B1 | 9/2005 | Chamberlin et al. |
| 6,948,843 | B2 | 9/2005 | Laugham, Jr. et al. |
| 7,034,143 | B1 | 4/2006 | Preparata et al. |
| 7,041,481 | B2 | 5/2006 | Anderson et al. |
| 7,049,077 | B2 | 5/2006 | Yang |
| 7,057,026 | B2 | 6/2006 | Barnes et al. |
| 7,071,324 | B2 | 7/2006 | Preparata et al. |
| 7,074,564 | B2 | 7/2006 | Landegren |
| 7,074,586 | B1 | 7/2006 | Cheronis et al. |
| 7,115,400 | B1 | 10/2006 | Adessi et al. |
| 7,169,560 | B2 | 1/2007 | Lapidus et al. |
| 7,211,390 | B2 | 5/2007 | Rothberg et al. |
| 7,232,656 | B2 | 6/2007 | Balasubramanian et al. |
| 7,244,559 | B2 | 7/2007 | Rothberg et al. |
| RE39,793 | E | 8/2007 | Brenner |
| 7,264,929 | B2 | 9/2007 | Rothberg et al. |
| 7,282,337 | B1 | 10/2007 | Harris |
| 7,297,518 | B2 | 11/2007 | Quake et al. |
| 7,320,860 | B2 | 1/2008 | Landegren et al. |
| 7,323,305 | B2 | 1/2008 | Leamon et al. |
| 7,335,762 | B2 | 2/2008 | Rothberg et al. |
| 7,351,528 | B2 | 4/2008 | Landegren |
| 7,393,665 | B2 | 7/2008 | Brenner |
| 7,510,829 | B2 | 3/2009 | Faham et al. |
| 7,523,117 | B2 | 4/2009 | Zhang et al. |
| 7,537,889 | B2 | 5/2009 | Sinha et al. |
| 7,537,897 | B2 | 5/2009 | Brenner et al. |
| 7,544,473 | B2 | 6/2009 | Brenner |
| 7,582,431 | B2 | 9/2009 | Drmanac et al. |
| 7,598,035 | B2 | 10/2009 | Macevicz |
| 7,629,151 | B2 | 12/2009 | Gold et al. |
| 7,642,056 | B2 | 1/2010 | Ahn et al. |
| 7,645,576 | B2 | 1/2010 | Lo et al. |
| 7,666,593 | B2 | 2/2010 | Lapidus |
| 7,700,323 | B2 | 4/2010 | Willis et al. |
| 7,774,962 | B2 | 8/2010 | Ladd |
| 7,776,616 | B2 | 8/2010 | Heath et al. |
| RE41,780 | E | 9/2010 | Anderson et al. |
| 7,790,388 | B2 | 9/2010 | Landegren et al. |
| 7,809,509 | B2 | 10/2010 | Milosavljevic |
| 7,835,871 | B2 | 11/2010 | Kain et al. |
| 7,838,223 | B2 | 11/2010 | Rivkees et al. |
| 7,883,849 | B1 | 2/2011 | Dahl |
| 7,957,913 | B2 | 6/2011 | Chinitz et al. |
| 7,960,120 | B2 | 6/2011 | Rigatti et al. |
| 7,985,716 | B2 | 7/2011 | Yershov et al. |
| 7,993,880 | B2 | 8/2011 | Willis et al. |
| 8,024,128 | B2 | 9/2011 | Rabinowitz et al. |
| 8,165,821 | B2 | 4/2012 | Zhang |
| 8,209,130 | B1 | 6/2012 | Kennedy et al. |
| 8,283,116 | B1 | 10/2012 | Bhattacharyya et al. |
| 8,462,161 | B1 | 6/2013 | Barber |
| 8,463,895 | B2 | 6/2013 | Arora et al. |
| 8,474,228 | B2 | 7/2013 | Adair et al. |
| 8,496,166 | B2 | 7/2013 | Burns et al. |
| 8,529,744 | B2 | 9/2013 | Marziali et al. |
| 8,778,609 | B1 | 7/2014 | Umbarger |
| 8,812,422 | B2 | 8/2014 | Nizzari et al. |
| 8,847,799 | B1 | 9/2014 | Kennedy et al. |
| 8,862,999 | B2 | 10/2014 | Gupta et al. |
| 8,865,534 | B2 | 10/2014 | Yamazaki |
| 8,976,049 | B2 | 3/2015 | Kennedy et al. |
| 9,074,244 | B2 | 7/2015 | Sparks et al. |
| 9,228,233 | B2 | 1/2016 | Kennedy et al. |
| 9,292,527 | B2 | 3/2016 | Kennedy et al. |
| 9,535,920 | B2 | 1/2017 | Kennedy et al. |
| 9,567,639 | B2 | 2/2017 | Oliphant et al. |
| 9,598,730 | B2 | 3/2017 | Del-Favero et al. |
| 2001/0007742 | A1 | 7/2001 | Landergren |
| 2001/0046673 | A1 | 11/2001 | French et al. |
| 2002/0001800 | A1 | 1/2002 | Lapidus |
| 2002/0040216 | A1 | 4/2002 | Dumont et al. |
| 2002/0091666 | A1 | 7/2002 | Rice et al. |
| 2002/0164629 | A1 | 11/2002 | Quake et al. |
| 2002/0182609 | A1 | 12/2002 | Arcot |
| 2002/0187496 | A1 | 12/2002 | Andersson et al. |
| 2003/0166057 | A1 | 9/2003 | Hildebrand et al. |
| 2003/0175709 | A1 | 9/2003 | Murphy et al. |
| 2003/0177105 | A1 | 9/2003 | Xiao et al. |
| 2003/0190663 | A1 | 10/2003 | Yang et al. |
| 2003/0203370 | A1 | 10/2003 | Yakhini et al. |
| 2003/0208454 | A1 | 11/2003 | Rienhoff et al. |
| 2003/0224384 | A1 | 12/2003 | Sayood et al. |
| 2004/0029264 | A1 | 2/2004 | Robbins |
| 2004/0106112 | A1 | 6/2004 | Nilsson et al. |
| 2004/0142325 | A1 | 7/2004 | Mintz et al. |
| 2004/0152108 | A1 | 8/2004 | Keith et al. |
| 2004/0170965 | A1 | 9/2004 | Scholl et al. |
| 2004/0171051 | A1 | 9/2004 | Holloway |
| 2004/0197813 | A1 | 10/2004 | Hoffman et al. |
| 2004/0209299 | A1 | 10/2004 | Pinter et al. |
| 2005/0003369 | A1 | 1/2005 | Christians et al. |
| 2005/0026204 | A1 | 2/2005 | Landegren |
| 2005/0032095 | A1 | 2/2005 | Wigler et al. |
| 2005/0048505 | A1 | 3/2005 | Fredrick et al. |
| 2005/0059048 | A1 | 3/2005 | Gunderson et al. |
| 2005/0100900 | A1 | 5/2005 | Kawashima et al. |
| 2005/0112590 | A1 | 5/2005 | Boom et al. |
| 2005/0186589 | A1 | 8/2005 | Kowalik et al. |
| 2005/0214811 | A1 | 9/2005 | Margulies et al. |
| 2005/0244879 | A1 | 11/2005 | Schumm et al. |
| 2005/0272065 | A1 | 12/2005 | Lakey et al. |
| 2006/0019304 | A1 | 1/2006 | Hardenbol et al. |
| 2006/0024681 | A1 | 2/2006 | Smith et al. |
| 2006/0078894 | A1 | 4/2006 | Winkler et al. |
| 2006/0149047 | A1 | 7/2006 | Nanduri et al. |
| 2006/0177837 | A1 | 8/2006 | Borozan et al. |
| 2006/0183132 | A1 | 8/2006 | Fu et al. |
| 2006/0192047 | A1 | 8/2006 | Goossen |
| 2006/0195269 | A1 | 8/2006 | Yeatman et al. |
| 2006/0292585 | A1 | 12/2006 | Nautiyal et al. |
| 2006/0292611 | A1 | 12/2006 | Berka et al. |
| 2007/0020640 | A1 | 1/2007 | McCloskey et al. |
| 2007/0042369 | A1 | 2/2007 | Reese et al. |
| 2007/0092883 | A1 | 4/2007 | Schouten et al. |
| 2007/0114362 | A1 | 5/2007 | Feng et al. |
| 2007/0128624 | A1 | 6/2007 | Gormley et al. |
| 2007/0161013 | A1 | 7/2007 | Hantash |
| 2007/0162983 | A1 | 7/2007 | Hesterkamp et al. |
| 2007/0166705 | A1 | 7/2007 | Milton et al. |
| 2007/0225487 | A1 | 9/2007 | Nilsson et al. |
| 2007/0238122 | A1 | 10/2007 | Allbritton et al. |

(56) References Cited

U.S. PATENT DOCUMENTS

| | | |
|---|---|---|
| 2007/0244675 A1 | 10/2007 | Shai et al. |
| 2007/0264653 A1 | 11/2007 | Berlin et al. |
| 2008/0003142 A1 | 1/2008 | Link et al. |
| 2008/0014589 A1 | 1/2008 | Link et al. |
| 2008/0076118 A1 | 3/2008 | Tooke et al. |
| 2008/0081330 A1 | 4/2008 | Kahvejian |
| 2008/0085836 A1 | 4/2008 | Kearns et al. |
| 2008/0090239 A1 | 4/2008 | Shoemaker et al. |
| 2008/0176209 A1 | 7/2008 | Muller et al. |
| 2008/0269068 A1 | 10/2008 | Church et al. |
| 2008/0280955 A1 | 11/2008 | McCamish |
| 2008/0293589 A1 | 11/2008 | Shapero |
| 2009/0009904 A1 | 1/2009 | Yasuna et al. |
| 2009/0019156 A1 | 1/2009 | Mo et al. |
| 2009/0026082 A1 | 1/2009 | Rothberg et al. |
| 2009/0029385 A1 | 1/2009 | Christians et al. |
| 2009/0042206 A1 | 2/2009 | Schneider et al. |
| 2009/0098551 A1 | 4/2009 | Landers et al. |
| 2009/0099041 A1 | 4/2009 | Church et al. |
| 2009/0105081 A1 | 4/2009 | Rodesch et al. |
| 2009/0119313 A1 | 5/2009 | Pearce |
| 2009/0127589 A1 | 5/2009 | Rothberg et al. |
| 2009/0129647 A1 | 5/2009 | Dimitrova et al. |
| 2009/0156412 A1 | 6/2009 | Boyce, IV et al. |
| 2009/0163366 A1 | 6/2009 | Nickerson et al. |
| 2009/0181389 A1 | 7/2009 | Li et al. |
| 2009/0191565 A1 | 7/2009 | Lapidus et al. |
| 2009/0192047 A1 | 7/2009 | Parr et al. |
| 2009/0202984 A1 | 8/2009 | Cantor |
| 2009/0203014 A1 | 8/2009 | Wu et al. |
| 2009/0226975 A1 | 9/2009 | Sabot et al. |
| 2009/0233814 A1 | 9/2009 | Bashkirov et al. |
| 2009/0298064 A1 | 12/2009 | Batzoglou et al. |
| 2009/0301382 A1 | 12/2009 | Patel |
| 2009/0318310 A1 | 12/2009 | Liu et al. |
| 2010/0035243 A1 | 2/2010 | Muller et al. |
| 2010/0035252 A1 | 2/2010 | Rothberg et al. |
| 2010/0063742 A1 | 3/2010 | Hart et al. |
| 2010/0069263 A1 | 3/2010 | Shendure et al. |
| 2010/0086926 A1 | 4/2010 | Craig et al. |
| 2010/0105107 A1 | 4/2010 | Hildebrand et al. |
| 2010/0137143 A1 | 6/2010 | Rothberg et al. |
| 2010/0137163 A1 | 6/2010 | Link et al. |
| 2010/0143908 A1 | 6/2010 | Gillevet |
| 2010/0159440 A1 | 6/2010 | Messier et al. |
| 2010/0188073 A1 | 7/2010 | Rothberg et al. |
| 2010/0196911 A1 | 8/2010 | Hoffman et al. |
| 2010/0197507 A1 | 8/2010 | Rothberg et al. |
| 2010/0216151 A1 | 8/2010 | Lapidus et al. |
| 2010/0216153 A1 | 8/2010 | Lapidus et al. |
| 2010/0248984 A1 | 9/2010 | Shaffer et al. |
| 2010/0282617 A1 | 11/2010 | Rothberg et al. |
| 2010/0285578 A1 | 11/2010 | Selden et al. |
| 2010/0297626 A1 | 11/2010 | McKernan et al. |
| 2010/0300559 A1 | 12/2010 | Schultz et al. |
| 2010/0300895 A1 | 12/2010 | Nobile et al. |
| 2010/0301042 A1 | 12/2010 | Kahlert |
| 2010/0301398 A1 | 12/2010 | Rothberg et al. |
| 2010/0304982 A1 | 12/2010 | Hinz et al. |
| 2010/0311061 A1 | 12/2010 | Korlach et al. |
| 2010/0330619 A1 | 12/2010 | Willis et al. |
| 2011/0004413 A1 | 1/2011 | Carnevali et al. |
| 2011/0009278 A1 | 1/2011 | Kain et al. |
| 2011/0015863 A1 | 1/2011 | Pevzner et al. |
| 2011/0021366 A1 | 1/2011 | Chinitz et al. |
| 2011/0034342 A1 | 2/2011 | Fox |
| 2011/0092375 A1 | 4/2011 | Zamore et al. |
| 2011/0098193 A1 | 4/2011 | Kingsmore et al. |
| 2011/0117544 A1 | 5/2011 | Lexow |
| 2011/0159499 A1 | 6/2011 | Hindson et al. |
| 2011/0166029 A1 | 7/2011 | Margulies et al. |
| 2011/0224105 A1 | 9/2011 | Kurn et al. |
| 2011/0230365 A1 | 9/2011 | Rohlfs et al. |
| 2011/0257889 A1 | 10/2011 | Klammer et al. |
| 2011/0288780 A1 | 11/2011 | Rabinowitz et al. |
| 2011/0301042 A1 | 12/2011 | Steinmann et al. |
| 2012/0015050 A1 | 1/2012 | Abkevich et al. |
| 2012/0021930 A1 | 1/2012 | Schoen et al. |
| 2012/0046877 A1 | 2/2012 | Hyland et al. |
| 2012/0059594 A1 | 3/2012 | Hatchwell et al. |
| 2012/0074925 A1 | 3/2012 | Oliver |
| 2012/0079980 A1 | 4/2012 | Taylor et al. |
| 2012/0115736 A1 | 5/2012 | Bjornson et al. |
| 2012/0164630 A1 | 6/2012 | Porreca et al. |
| 2012/0165202 A1 | 6/2012 | Porreca et al. |
| 2012/0179384 A1 | 7/2012 | Kuramitsu et al. |
| 2012/0214678 A1 | 8/2012 | Rava |
| 2012/0216151 A1 | 8/2012 | Sarkar et al. |
| 2012/0236861 A1 | 9/2012 | Ganeshalingam et al. |
| 2012/0245041 A1 | 9/2012 | Brenner et al. |
| 2012/0252020 A1 | 10/2012 | Shuber |
| 2012/0252684 A1 | 10/2012 | Selifonov et al. |
| 2012/0258461 A1 | 10/2012 | Weisbart |
| 2012/0270212 A1 | 10/2012 | Rabinowitz et al. |
| 2012/0270739 A1 | 10/2012 | Rava et al. |
| 2013/0085082 A1 | 4/2013 | Vermeesch et al. |
| 2013/0130921 A1 | 5/2013 | Gao et al. |
| 2013/0178378 A1 | 7/2013 | Hatch et al. |
| 2013/0183672 A1 | 7/2013 | de Laat et al. |
| 2013/0222388 A1 | 8/2013 | McDonald |
| 2013/0268474 A1 | 10/2013 | Nizzari et al. |
| 2013/0275103 A1 | 10/2013 | Struble et al. |
| 2013/0288242 A1 | 10/2013 | Stoughton et al. |
| 2013/0323730 A1 | 12/2013 | Curry et al. |
| 2013/0332081 A1 | 12/2013 | Reese et al. |
| 2013/0344096 A1 | 12/2013 | Chiang et al. |
| 2014/0129201 A1 | 5/2014 | Kennedy et al. |
| 2014/0136120 A1 | 5/2014 | Colwell et al. |
| 2014/0206552 A1 | 7/2014 | Rabinowitz et al. |
| 2014/0222349 A1 | 8/2014 | Higgins et al. |
| 2014/0228226 A1 | 8/2014 | Yin et al. |
| 2014/0318274 A1 | 10/2014 | Zimmerman et al. |
| 2014/0361022 A1 | 12/2014 | Finneran |
| 2015/0051085 A1 | 2/2015 | Vogelstein et al. |
| 2015/0056613 A1 | 2/2015 | Kural |
| 2015/0178445 A1 | 6/2015 | Cibulskis et al. |
| 2015/0299767 A1 | 10/2015 | Armour et al. |
| 2016/0034638 A1 | 2/2016 | Spence et al. |
| 2016/0210404 A1 | 7/2016 | Umbarger et al. |
| 2016/0210486 A1 | 7/2016 | Porreca et al. |
| 2017/0044610 A1 | 2/2017 | Johnson |
| 2017/0129964 A1 | 5/2017 | Cheung |
| 2021/0090687 A1 | 3/2021 | Umbarger et al. |

FOREIGN PATENT DOCUMENTS

| | | |
|---|---|---|
| EP | 10770071.8 | 11/2010 |
| EP | 2 425 240 A2 | 3/2012 |
| EP | 2 437 191 A2 | 4/2012 |
| EP | 2 716 766 A1 | 4/2014 |
| JP | 2008-518639 A | 6/2008 |
| JP | 2014-530024 A | 11/2014 |
| WO | WO 95/011995 A1 | 5/1995 |
| WO | WO 96/019586 A1 | 6/1996 |
| WO | WO 98/014275 A1 | 4/1998 |
| WO | WO 98/044151 A1 | 10/1998 |
| WO | WO 00/18957 A1 | 4/2000 |
| WO | WO 00/28085 A1 | 5/2000 |
| WO | WO 02/093453 A2 | 11/2002 |
| WO | WO 2004/015609 A2 | 2/2004 |
| WO | WO 2004/018497 A2 | 3/2004 |
| WO | WO 2004/083819 A2 | 9/2004 |
| WO | WO 2005/003304 A2 | 1/2005 |
| WO | WO 2007/010251 A2 | 1/2007 |
| WO | WO 2007/107717 A1 | 9/2007 |
| WO | WO 2007/123744 A2 | 11/2007 |
| WO | WO 2007/135368 A2 | 11/2007 |
| WO | WO 2008/067551 A2 | 6/2008 |
| WO | WO 2009/036525 A2 | 3/2009 |
| WO | WO 2010/024894 A1 | 3/2010 |
| WO | WO 2010/126614 A2 | 11/2010 |
| WO | WO 2011/006020 A1 | 1/2011 |
| WO | WO 2011/102998 A2 | 8/2011 |
| WO | WO 2011/157846 A1 | 12/2011 |

(56) References Cited

FOREIGN PATENT DOCUMENTS

| WO | WO 2012/006291 A2 | 1/2012 |
|----|-------------------|--------|
| WO | WO 2012/040387 A1 | 3/2012 |
| WO | WO 2012/051208 A2 | 4/2012 |
| WO | WO 2012/087736 A1 | 6/2012 |
| WO | WO 2012/109500 A2 | 8/2012 |
| WO | WO 2012/134884 A1 | 10/2012 |
| WO | WO 2012/149171 A1 | 11/2012 |
| WO | WO 2012/170725 A2 | 12/2012 |
| WO | WO 2013/052557 A2 | 4/2013 |
| WO | WO 2013/058907 A1 | 4/2013 |
| WO | WO 2013/148496 A1 | 10/2013 |
| WO | WO 2013/177086 A1 | 11/2013 |
| WO | WO 2013/191775 A2 | 12/2013 |
| WO | WO 2014/074246 A1 | 5/2014 |
| WO | WO 2015/089333 A1 | 6/2015 |

OTHER PUBLICATIONS

Adey, 2010, Rapid, low-input, low-bias construction of shotgun fragment libraries by high-density in vitro transposition, Genome Biol 11:R119.

Ageno et al., 1969, The alkaline denaturation of DNA, Biophys J 9(11):1281-1311.

Agrawal, 1990, Site-specific functionalization of oligodeoxynucleotides for non-radioactive labelling, Tetrahedron Let 31:1543-1546.

Akhras et al., 2007, Connector Inversion Probe Technology: A Powerful OnePrimer Multiplex DNA Amplification System for Numerous Scientific Applications, PLOS ONE 2(9):e915.

Alazard et al., 2002, Sequencing of production-scale synthetic oligonucleotides by enriching for coupling failures using matrix-assisted laser desorption/ionization time-of-flight mass spectrometry, Analytical biochemistry 301:57-64.

Albert, 2007, Direct selection of human genomic loci by microarray hybridization, Nature Methods 4(11):903-5.

Aljanabi and Martinez, 1997, Universal and rapid salt-extraction of high quality genomic DNA for PCR-based techniques, Nucl. Acids Res 25:4692-4693.

Antonarakis and the Nomenclature Working Group, 1998, Recommendations for a nomenclature system for human gene mutations, Human Mutation 11:1-3.

Archer, 2014, Selective and flexible depletion of problematic sequences from RNA-seq libraries at the cDNA stage, BMC Genomics 15(1):401.

Ball et al., 2009, Targeted and genome-scale strategies reveal gene-body methylation signatures in human cells, Nat Biotech 27:361-8.

Balzer, 2013, Filtering duplicate reads from 454 pyrosequencing data, Bioinformatics 29(7):830-836.

Barany, 1991, Genetic disease detection and DNA amplification using cloned thermostable ligase, PNAS 88:189-193.

Barany, 1991, The Ligase Chain Reaction in a PCR World, Genome Research 1:5-16.

Bau et al., 2008, Targeted next-generation sequencing by specific capture of multiple genomic loci using low-volume microfluidic DNA arrays, Analytical and Bioanal Chem 393(1):171-5.

Beer, 1962, Determination of base sequence in nucleic acids with the electron microscope: visibility of a marker, PNAS 48(3):409-416.

Bell et al., 2011, Carrier testing for severe childhood recessive diseases by next-generation sequencing, Science Translational Medicine 3(65ra4), 15 pages.

Benner et al., 2001, Evolution, language and analogy in functional genomics, Trends Genet 17:414-8.

Bentzley et al., 1996, Oligonucleotide sequence and composition determined by matrix-assisted laser desorption/ionization, Anal Chem 68:2141-2146.

Bentzley et al., 1998, Base specificity of oligonucleotide digestion by calf spleen phosphodiesterase with matrix-assisted laser desorption ionization analysis, Anal Biochem 258:31-37.

Bickle & Kruger, 1993, Biology of DNA Restriction, Microbiol Rev 57(2):434-50.

Bonfield, 2013, Compression of FASTQ and SAM format sequencing data, PLoS One 8(3):e59190.

Bose, 2012, BIND—An algorithm for loss-less compression of nucleotide sequence data, J Biosci 37(4):785-789.

Boyden, 2013, High-throughput screening for SMN1 copy number loss by next-generation sequencing, American Society of Human Genetics 63rd Annual Meeting, Abstract, Oct. 22, 2013 (2 pages).

Boyer, 1971, DNA restriction and modification mechanisms in bacteria, Ann Rev Microbiol 25:153-76.

Braasch and Corey, 2001, Locked nucleic acid (LNA): fine-tuning the recognition of DNA and RNA, Chemistry & Biology 8(1):1-7.

Braslavsky, 2003, Sequence information can be obtained from single DNA molecules, PNAS 100:3960-4.

Brezina, 2010, Single-gene testing combined iwth single nucleotide polymorphism microarray preimplantatoin genetic diagnosis for aneuploidy, Fert Stert 95(5):1786e5-e8.

Brinkman, 2004, Splice Variants as Cancer Biomarkers, Clin Biochem 37:584.

Brown et al., 1979, Chemical synthesis and cloning of a tyrosine tRNA gene, Methods Enzymol 68:109-51.

Browne, 2002, Metal ion-catalyzed nucleic Acid alkylation and fragmentation, J Am Chem Soc 124(27):7950-7962.

Brownstein, 2014, An international effort towards developing standards for best practices in analysis, interpretation and reporting of clinical genome sequencing results in the CLARITY Challenge, Genome Biol 15:R53.

Bunyan et al., 2004, Dosage analysis of cancer predisposition genes by multiplex ligation-dependent probe amplification, British Journal of Cancer, 91(6):1155-59.

Burrow & Wheeler, 1994, A block-sorting lossless data compression algorithm, Technical Report 124, Digital Equipment Corporation, CA.

Carpenter, 2013, Pulling out the 1%: whole-genome capture for the targeted enrichment of ancient DNA sequencing libraries, Am J Hum Genet 93(5):852-864.

Caruthers, 1985, Gene synthesis machines: DNA chemistry and its uses, Science 230:281-285.

Castellani, 2008, Consenses on the use of and interpretation of cystic fibrosis mutation analysis in clinical practice, J Cyst Fib 7:179-196.

CDC, 2011, Assisted Reproductive Technology: Fertility Clinic Success Rates Report.

Challis, 2012, An integrative variant analysis suite for whole exome next-generation sequencing data, BMC Informatics 13(8):1-12.

Chan et al., 2011, Natural and engineered nicking endonucleases—from cleavage mechanism to engineering of strand-specificity, Nucl Acids Res 39(1):1-18.

Chen, 2010, Identification of racehorse and sample contamination by novel 24-plex STR system, Forensic Sci Int: Genetics 4:158-167.

Chennagiri, 2013, A generalized scalable database model for storing and exploring genetic variations detected using sequencing data, American Society of Human Genetics 63rd Annual Meeting, Abstract, Oct. 22, 2013 (2 pages).

Chevreux et al., 1999, Genome Sequence Assembly Using Trace Signals and Additional Sequence Information, Computer Science and Biology: Proceedings of the German Conference on Bioinformatics (GCB) 99:45-56.

Chirgwin et al., 1979, Isolation of biologically active ribonucleic acid from sources enriched in ribonuclease, Biochemistry, 18:5294-99.

Choe et al., 2010, Novel CFTR Mutations in a Korean Infant with Cystic Fibrosis and Pancreatic Insufficiency, J Korean Med Sci 25:163-5.

Ciotti et al., 2004, Triplet Repeat Primed PCR (TP PCR) in Molecular Diagnostic Testing for Friedrich Ataxia, Journal of Molecular Diagnostics 6(4):285-9.

Cock et al., 2010, The Sanger FASTQ file format for sequences with quality scores, and the Solexa/Illumina FASTQ variants, Nucleic Acids Res 38(6):1767-1771.

Collins et al., 2004, Finishing the euchromatic sequence of the human genome, Nature 431 (7011):931-45.

(56)     References Cited

OTHER PUBLICATIONS

Cremers, 1998, Autosomal Recessive Retinitis Pigmentosa and Cone-Rod Dystrophy Caused by Splice Site Mutations in the Stargardt's Disease Gene ABCR, Hum Mol Gen 7(3):355.

Cronin, 1996, Cystic Fibrosis Mutation Detection by Hybridization to Light-Generated DNA Probe Arrays, Human Mutation 7:244.

Dahl et al., 2005, Multiplex amplification enabled by selective circularization of large sets of genomic DNA fragments, Nucleic Acids Res 33(8):e71.

Danecek et al., 2011, The variant call format and VCFtools, Bioinformatics 27(15):2156-2158.

De la Bastide & McCombie, 2007, Assembling genome DNA sequences with PHRAP, Current Protocols in Bioinformatics 17:11.4.1-11.4.15.

Delcher et al., 1999, Alignment of whole genomes, Nuc Acids Res 27(11):2369-2376.

Den Dunnen & Antonarakis, 2003, Mutation Nomenclature, Curr Prot Hum Genet 7.13.1-7.13.8.

Deng et al., 2009, Targeted bisulfite sequencing reveals changes in DNA methylation associated with nuclear reprogramming, Nature Biotechnology 27:353-60 (and supplement).

Deng et al., 2012, Supplementary Material, Nature Biotechnology, S1-1-S1-11, Retrieved from the Internet on Oct. 24, 2012.

Deorowicz, 2013, Data compression for sequencing data, Alg for Molec Bio 8:25.

Diep, 2012, Library-free methylation sequencing with bisulfite padlock probes, Nature Methods 9:270-272 (and supplemental information).

DiGuistini et al., 2009, De novo genome sequence assembly of a filamentous fungus using Sanger, 454 and Illumina sequence data, Genome Biology 10:R94.

Dolinsek, 2013, Depletion of unwanted nucleic acid templates by selection cleavage: LNAzymes, catalytically active oligonucleotides containing locked nucleic acids, open a new window for detecting rare microbial community members, App Env Microbiol 79(5): 1534-1544.

Dong & Yu, 2011, Mutation surveyor: An in silico tool for sequencing analysis, Methods Mol Biol 760:223-37.

Drmanac, 1992, Sequencing by hybridization: towards an automated sequencing of one million M13 clones arrayed on membranes, Electrophoresis 13:566-573.

Dudley et al., 2009, A Quick Guide for Developing Effective Bioinformatics Programming Skills, PLOS Comput Biol 5(12):e1000589.

Ericsson, 2008, A dual-tag microarray platform for high-performance nucleic acid and protein analyses, Nucl Acids Res 36:e45.

Fares, et al., 2008, Carrier frequency of autosomal-recessive disorders in the Ashkenazi Jewish population: should the rationale for mutation choice for screening be reevaluated?, Prenatal Diagnosis 28:236-41.

Faulstich et al., 1997, A sequencing method for RNA oligonucleotides based on mass spectrometry, Anal Chem 59:4349-4353.

Faust, 2014, SAMBLASTER: fast duplicate marking and structural variant read extraction, Bioinformatics published online May 7, 2014.

Fitch, 1970, Distinguishing homologs from analogous proteins, Syst Biol 19(2):99-113.

Frey, Bruce, 2006, Statistics Hacks 108-115.

Friedenson, 2005, BRCA1 and BRCA2 Pathways and the Risk of Cancers Other Than Breast or Ovarian, Medscape General Medicine 7(2):60.

Furtado et al., 2011, Characterization of large genomic deletions in the FBN1 gene using multiplex ligation-dependent probe amplification, BMC Medical Genetics 12:119 (7 pages).

Garber, 2008, Fixing the front end, Nature Biotechnology 26(10):1101-04.

Gemayel et al., 2010, Variable Tandem Repeats Accelerate Evolution of Coding and Regulatory Sequences, Annual Review of Genetics 44:445-77.

Giusti, 1993, Synthesis and Characterization of f'-Fluorescent-dye-labeled Oligonucleotides, PCR Meth Appl 2:223-227.

Glover et al., 1995, Sequencing of oligonucleotides using high performance liquid chromatography and electrospray mass spectrometry, Rapid Com Mass Spec 9:897-901.

Gnirke et al., 2009, Solution hybrid selection with ultra-long oligonucleotides for massively parallel targeted sequencing, Nature Biotechnology 27:182-9.

Goto, 2010, BioRuby: bioinformatics software for the Ruby programming language, Bioinformatics 26(20):2617-2619.

Goto, 1994, A Study on Development of a Deductive Object-Oriented Database and its Application to Genome Analysis, PhD Thesis, Kyushu University, Kyushu, Japan (106 pages).

Green, 2005, Suicide polymerase endonuclease restriction, a novel technique for enhancing PCR amplification of minor DNA template, Appl Env Microbiol 71(8):4721-4727.

Guerrero-Fernandez, 2013, FQbin: a compatible and optimized format for storing and managing sequence data, WBBIO Proceedings, Granada 337-344.

Gupta, 1991, A general method for the synthesis of 3'-sulfhydryl and phosphate group containing oligonucleotides, Nucl Acids Res 19(11):3019-3025.

Gut & Beck, 1995, A procedure for selective DNA alkylation and detection by mass spectrometry, Nucl Acids Res 23(8):1367-1373.

Hallam, 2014, Validation for clinical use of, and initial clinical experience with, a novel approach to population-based carrier screening using high-throughput, next-generation DNA sequencing, J Mol Diagn 16:180-89.

Hammond et al., 1996, Extraction of DNA from preserved animal specimens for use in randomly amplified polymorphic DNA analysis, An Biochem 240:298-300.

Hardenbol et al., 2005, Highly multiplexed molecular inversion probe genotyping: over 10,000 targeted SNPs genotyped in a single tube assay, Genome Res 15:269-75.

Hardenbol et al., 2003, Multiplexed genotyping with sequence-tagged molecular inversion probes, Nature Biotechnology 21:673-8.

Harris & Kiang, 2006, Defects can increase the melting temperature of DNA-nanoparticle assemblies, J Phys Chem B 110(33):16393-6.

Harris, 2008, Helicos True Single Molecule Sequencing (tSMS), Science 320:106-109.

Harris et al., 2008, Single-molecule DNA sequencing of a viral genome, Science 320(5872):106-9.

Heger, 2006, Protonation of Cresol Red in Acidic Aqueous Solutions Caused by Freezing, J Phys Chem B 110(3):1277-1287.

Heid, 1996, Real time quantitative PCR, Genome Res 6:986-994.

Hiatt et al., 2013, Single molecule molecular inversion probes for targeted, high-accuracy detection of low-frequency variation, Genome Research 23:843-54.

Hodges et al., 2007, Genome-wide in situ exon capture for selective resequencing, Nat Genet 39(12):1522-7.

Holland, 2008, BioJava: an open-source framework for bioinformatics, Bioinformatics 24(18):2096-2097.

Homer et al., 2008, Resolving Individuals Contributing Trace Amounts of DNA to Highly Complex Mixtures Using High-Density SNP Genotyping Microarrays, PLoS One 4(8):e1000167.

Homer, 2009, BFAST: An alignment tool for large scale genome resequencing, PLoS ONE 4(11 ):e7767.

Housley, 2009, SNP discovery and haplotype analysis in the segmentally duplicated DRD5 coding region, Ann Hum Genet 73(3):274-282.

Huang et al., 2008, Comparative analysis of common CFTR polymorphisms poly-T, TGrepeats and M470V in a healthy Chinese population, World J Gastroenterol 14(12):1925-30.

Husemann & Stoye, 2009, Phylogenetic Comparative Assembly, Algorithms in Bioinformatics: 9th International Workshop, pp. 145-156, Salzberg & Warnow, Eds. Springer-Verlag, Berlin, Heidelberg.

Illumina, 2010, De Novo assembly using Illumina reads, Technical Note (8 pages).

International Human Genome Sequencing Consortium, 2004, Finishing the euchromatic sequence of the human genome, Nature 431:931-945.

Iqbal et al., 2012, De novo assembly and genotyping of variants using colored de Bruijn graphs, Nature Genet 44(2):226-232.

(56)           References Cited

OTHER PUBLICATIONS

Isosomppi, 2009, Disease-causing mutations in the CLRNI gene alter normal CLRN1 protien trafficking to the plasma membrane, Mol Vis 15:1806-1818.

Jaijo et al., 2010, Microarray-based mutation analysis of 183 Spanish families with Usher syndrome, Invest Ophthalmo Vis Sci 51(3):1311-7.

Jensen, 2001, Orthologs and paralogs—we need to get it right, Genome Biol 2(8):1002-1002.3.

Jones et al., 2008, Core Signaling Pathways in Human Pancreatic Cancers Revealed by Global Genomic Analyses, Science 321(5897):1801-1806.

Kambara et al., 1988, Optimization of Parameters in a DNA Sequenator Using Fluorescence Detection, Nature Biotechnology 6:816-821.

Kennedy et al., 2013, Accessing more human genetic variation with short sequencing reads, American Society of Human Genetics 63rd Annual Meeting, Abstract, Oct. 22, 2013 (2 pages).

Kent, 2002, BLAT—The BLAST-like alignment tool, Genome Res 12(4):656-664.

Kerem, 1989, Identification of the cystic fibrosis gene: genetic analysis, Science 245:1073-1080.

Kinde, 2012, FAST-SeqS: a simple and effective method for detection of aneuploidy by massively parallel sequencing, PLoS One 7(7):e41162.

Kircher et al., 2010, High-througput DNA sequencing—concepts and limitations, Bioassays 32:524-36.

Kirpekar et al., 1994, Matrix assisted laser desorption/ionization mass spectrometry of enzymatically synthesized RNA up to 150 kDa, Nucleic Acids Res 22:3866-3870.

Klein et al., 2011, LOCAS—A low coverage sequence assembly tool for re-sequencing projects, PLoS One 6(8):article 23455.

Kneen, 1998, Green fluorescent protein as a noninvasive intracellular pH indicator, Biophys J 74(3):1591-99.

Koboldt et al., 2009, VarScan: variant detection in massively parallel sequencing of individual and pooled samples, Bioinformatics 25:2283-85.

Krawitz, 2010, Microindel detection in short-read sequence data, Bioinformatics 26(6):722-729.

Kreindler, 2010, Cystic fibrosis: exploiting its genetic basis in the hunt for new therapies, Pharmacol Ther 125(2):219-229.

Krishnakumar et al., 2008, A comprehensive assay for targeted multiplex amplification of human DNA sequences, PNAS 105:9296-301.

Kumar & Blaxter, 2010, Comparing de novo assemblers for 454 transcriptome data, Genomics 11:571.

Kurtz et al., 2004, Versatile and open software for comparing large genomes, Genome Biology, 5:R12.

Lam et al., 2008, Compressed indexing and local alignment of DNA, Bioinformatics 24(6):791-97.

Langmead et al., 2009, Ultrafast and memory-efficient alignment of short DNA sequences to the human genome, Genome Biology, 10:R25.

Larkin et al., 2007, Clustal W and Clustal X version 2.0, Bioinformatics 23(21):2947-2948.

Lecompte et al., 2001, Multiple alignment of complete sequences (MACS) in the post-genomic era, Gene 270(1-2):17-30.

Li & Durbin, 2009, Fast and accurate short read alignment with Burrows-Wheeler transform, Bioinformatics, 25(14):1754-60.

Li, 2003, DNA binding and cleavage by the periplasmic nuclease Vvn: a novel structure with a known active site, EMBO J 22(15):4014-4025.

Li et al., 2008, SOAP: short oligonucleotide alignment program, Bioinformatics 24(5):713-14.

Li, 2009, SOAP2: an improved ultrafast tool for short read alignment, Bioinformatics 25(15):1966-67.

Li, 2009, The Sequence Alignment/Map format and SAMtools, Bioinformatics 25(16):2078-9.

Li, 2010, Fast and accurate long-read alignment with Burrows-Wheeler transform, Bioinformatics 26(5):589-95.

Li, 2011, Improving SNP discovery by base alignment quality, Bioinformatics 27:1157.

Li et al., 2011, Single nucleotide polymorphism genotyping and point mutation detection by ligation on microarrays, J Nanosci Nanotechnol 11(2):994-1003.

Li, 2012, A new approach to detecting low-level mutations in next-generation sequence data, Genome Biol 13:1-15.

Li, 2014, HUGO: Hierarchical multi-reference Genome compression for aligned reads, JAMIA 21:363-373.

Lin et al., 2008, ZOOM! Zillions of Oligos Mapped, Bioinformatics 24:2431.

Lin, 2010, A molecular inversion prove assay for detecting alternative splicing, BMC Genomics 11(712):1-14.

Lin, et al., 2012, Development and evaluation of a reverse dot blot assay for the simultaneous detection of common alpha and beta thalassemia in Chinese, Blood Cells, Molecules and Diseases 48(2):86-90.

Lipman & Pearson, 1985, Rapid and sensitive protein similarity searches, Science 227(4693):1435-41.

Liu, 2012, Comparison of next-generation sequencing systems, J Biomed Biotech 2012:251364.

Llopis, 1998, Measurement of cytosolic, mitochondrial, and Golgi pH in single living cells with green fluorescent proteins, PNAS 95(12):6803-08.

Ma, 2006, Application of real-time polymerase chain reaction (RT-PCR), J Am Soc 1-15.

MacArthur, 2014, Guidelines for investigating causality of sequence variants in human disease, Nature 508:469-76.

Maddalena, 2005, Technical standards and guidelines: molecular genetic testing for ultra-rare disorders, Genet Med 7:571-83.

Malewicz, et al., 2010, Pregel: a system for large-scale graph processing, Proceedings ACM SIGMOD Int Conf Management Data 135-146.

Mamanova, 2010, Target-enrichment strategies for next generation sequencing, Nature Methods 7(2):111-8.

Margulies et al., 2005, Genome sequencing in microfabricated high-density picolitre reactors, Nature 437, Supplemental Material, 52 pages.

Margulies et al., 2005, Genome sequencing in microfabricated high-density picolitre reactors, Nature 437(7057):376-380.

Marras, 1999, Multiplex detection of single-nucleotide variations using molecular beacons, Genetic Analysis: Biomolecular Engineering 14:151.

Maxam & Gilbert, 1977, A new method for sequencing DNA, PNAS 74:560-564.

May 1988, How Many Species are There on Earth?, Science 241(4872):1441-9.

McKenna, 2010, The Genome Analysis Toolkit: a MapReduce framework for analyzing next-generation DNA sequencing data, Genome Res 20(9):1297-1303.

Meyer, 2007, Targeted high-throughput sequencing of tagged nucleic acid samples, Nucleic Acids Research 35(15):e97 (5 pages).

Meyer et al., 2008, Parallel tagged sequencing on the 454 platform, Nature Protocols 3(2):267-78.

Miesenbock, 1998, Visualizing secretion and synaptic transmission with pH-sensitive green fluorescent proteins, Nature 394(6689):192-95.

Miller, 2010, Assembly algorithms for next-generation sequencing data, Genomics 95:315-327.

Mills et al., 2010, Mapping copy number variation by population-scale genome sequencing, Nature 470(7332):59-65.

Miner, 2004, Molecular barcodes detect redundancy and contamination in hairpin-bisulfite PCR, Nucl Acids Res 32(17):e135.

Minton et al., 2011, Mutation Surveyor: Software for DNA Sequence Analysis, Methods in Molecular Biology 588:143-53.

Miyazaki et al., 2009, Characterization of deletion breakpoints in patients with dystrophinopathy carrying a deletion of exons 45-55 of the Duchenne muscular dystrophy (DMD) gene, Journal of Human Genetics 54:127-30.

Mockler et al., 2005, Applications of DNA tiling arrays for whole-genome analysis, Genomics 85(1):1-15.

(56) References Cited

OTHER PUBLICATIONS

Mohammed, 2012, DELIMINATE—a fast and efficient method for loss-less compression of genomic sequences, Bioinformatics 28(19):2527-2529.

Moudrianakis & Beer, 1965, Base sequence determination in nucleic acids with the electron microscope, PNAS 53:564-71.

Mullan, 2002, Multiple sequence alignment—the gateway to further analysis, Brief Bioinform 3(3):303-5.

Munne, 2012, Preimplantation genetic diagnosis for aneuploidy and translocations using array comparative genomic hybridization, Curr Genomics 13(6):463-470.

Nan et al., 2006, A novel CFTR mutation found in a Chinese patient with cystic fibrosis, Chinese Medical Journal 119(2):103-9.

Narang et al., 1979, Improved phosphotriester method for the synthesis of gene fragments, Methods Enzymol, 68:90.

Nelson, 1989, Bifunctional oligonucleotide probes synthesized using a novel CPG support are able to detect single base pair mutations, Nucl Acids Res 17(18):7187-7194.

Ng et al., 2009, Targeted capture and massively parallel sequencing of 12 human exomes, Nature 461(7261):272-6.

Nicholas et al., 2002, Strategies for multiple sequence alignment, Biotechniques 32:572-91.

Nickerson et al., 1990, Automated DNA diagnostics using an ELISA-based oligonucleotide ligation assay, Proc National Academy of Science 87:8923-7.

Nielsen et al., 1999, Peptide Nucleic Acids, Protocols and Applications (Norfolk: Horizon Scientific Press, 1-19).

Nilsson et al., 2006, Analyzing genes using closing and replicating circles, Trends in Biotechnology 24:83-8.

Ning, 2001, SSAHA: a fast search method for large DNA databases, Genome Res 11(10):1725-9.

Nordhoff et al., 1993, Ion stability of nucleic acids in infrared matrix-assisted laser desorption/ionization mass spectrometry, Nucl Acids Res 21(15):3347-57.

Nuttle, 2013, Rapid and accurate large-scale genotyping of duplicated genes and discovery of interlocus gene conversions, Nat Meth 10(9):903-909.

Nuttle et al., 2014, Resolving genomic disorder-associated breakpoints within segmental DNA duplications using massively parallel sequencing, Nature Protocols 9(6):1496-1513.

Oefner et al., 1996, Efficient random sub-cloning of DNA sheared in a recirculating point-sink flow system, Nucleic Acids Res 24(20):3879-3886.

Oka et al., 2006, Detection of loss of heterozygosity in the p53 gene in renal cell carcinoma and bladder cancer using the polymerase chain reaction, Molecular Carcinogenesis 4(1):10-13.

Okoniewski et al., 2013, Precise breakpoint localization of large genomic deletions using PacBio and Illumina next-generation sequencers, Biotechniques 54(2):98-100.

Oliphant et al., 2002, BeadArray technology: enabling an accurate, cost-effective approach to high-throughput genotyping, Biotechniques Suppl:56-8, 60-1.

O'Roak, 2012, Multiplex targeted sequencing identifies recurrently mutated genes in autism spectrum disorders, Science 338(6114):1619-1622.

Ordahl et al., 1976, Sheared DNA fragment sizing: comparison of techniques, Nucleic Acids Res 3:2985-2999.

Ostrer, 2001, A genetic profile of contemporary Jewish populations, Nat Rev Genet 2(11):891-8.

Owens et al., 1998, Aspects of oligonucleotide and peptide sequencing with MALDI and electrospray mass spectrometry, Bioorg Med Chem 6:1547-1554.

Parameswaran et al., 2007, A pyrosequencing-tailored nucleotide barcode design unveils opportunities for large-scale sample multiplexing, Nucleic Acids Research 35:e130, Supplementary Material, 18 pages.

Parameswaran et al., 2007, A pyrosequencing-tailored nucleotide barcode design unveils opportunities for large-scale sample multiplexing, Nucleic Acids Research 35:e130, Supplementary Material.

Parkinson, 2012, Preparation of high-quality next-generation sequencing libraries from picogram quantities of target DNA, Genome Res 22:125-133.

Pastor, 2010, Conceptual modeling of human genome mutations: a dichotomy between what we have and what we should have, 2010 Proc BIOSTEC Bioinformatics, pp. 160-166.

Paton, 2000, Conceptual modelling of genomic information, Bioinformatics 16(6):548-57.

Pearson & Lipman, 1988, Improved tools for biological sequence comparison, PNAS 85(8):2444-8.

Pertea et al., 2003, TIGR Gene indices clustering tools (TGICL): a software system for fast clustering of large EST datasets, Bioinformatics 19(5):651-52.

Pieles et al., 1993, Matrix-assisted laser desorption ionization time-of-flight mass spectrometry: a powerful tool for the mass and sequence analysis of natural and modified oligonucleotides, Nucleic Acids Res 21:3191-3196.

Pinho, 2013, MFCompress: a compression tool for FASTA and multi-FASTA data, Bioinformatics 30(1): 117-8.

Porreca et al., 2007, Multiplex amplification of large sets of human exons, Nat Methods 4:931-6.

Porreca et al., 2013, Analytical performance of a Next-Generation DNA sequencing- based clinical workflow for genetic carrier screening, American Society of Human Genetics 63rd Annual Meeting, Abstract, Oct. 22, 2013 (2 pages).

Procter et al., 2006, Molecular diagnosis of Prader-Willi and Angelman syndromes by methylation-specific melting analysis and methylation-specific multiplex ligation- dependent probe amplification, Clin Chem 52(7):1276-83.

Qiagen, 2011, Gentra Puregene handbook, 3d Ed. (72 pages).

Quail, 2010, DNA: Mechanical Breakage, In Encyclopedia of Life Sciences, John Wiley & Sons Ltd, Chicester (5 pages).

Rambaut et al., 1997, Seq-Gen: an application for the Monte Carlo simulation of DNA sequence evolution along phylogenetic trees, Bioinformatics (formerly CABIOS) 13:235-38.

Richards, 2008, ACMG recommendations for standards for interpretation and reporting of sequence variations: Revisions 2007, Genet Med 10:294-300.

Richter et al., 2008, MetaSim—A Sequencing Simulator for Genomics and Metagenomics, PLOS ONE 3:e3373.

Roberts, 1980, Restriction and modification enzymes and their recognition sequences, Nucleic Acids Res 8(1):r63-r80.

Robinson et al., 2013, Graph Databases, O'Reilly Media, Inc., Sebastopol, CA (223 pages).

Rodriguez and Neubauer, 2010, Constructions from Dots and Lines, Bulletin Am Soc Inf Sci Tech 36(6):35-41.

Rosendahl et al., 2013, CFTR, SPINK1, CTRC and PRSS1 variants in chronic pancreatitis: is the role of mutated CFTR overestimated?, Gut 62:582-592.

Rothberg et al., 2011, An integrated semiconductor device enabling non-optical genome sequencing, Nature 475:348-352.

Rowntree and Harris, 2003, The phenotypic consequences of CFTR mutations, Ann Hum Gen 67:471-485.

Gustincich et al., 1991, A fast method for high-quality genomic DNA extraction from whole human blood, Bio Techniques 11(3):298-302.

Saihan, 2009, Update on Usher syndrome, Curr Opin Neurology 22:19-27.

Sanger et al., 1977, DNA Sequencing with chain-terminating inhibitors, PNAS 74(12):5463-5467.

Santa Lucia, 1998, A unified view of polymer, dumbbell, and oligonucleotide DNA nearest-neighbor thermodynamics, PNAS 95(4):1460-5.

Sargent, 1988, Isolation of differentially expressed genes, Methods Enzymol 152:423-432.

Sauro, 2004, How do you Calculate a Z-Score/ Sigma Level?, https://www.measuringusability.com/zcalc.htm (online publication).

Sauro, 2004, What's a Z-Score and why use it in Usability Testing?, https://www.measuringusability.com/z.htm (online publication).

Schadt et al., 2010, A window into third-generation sequencing, Human Molecular Genetics 19(R2):R227-40.

(56) References Cited

OTHER PUBLICATIONS

Schatz et al., 2010, Assembly of large genomes using second-generation sequencing, Genome Res., 20:1165-1173.

Schiffman, 2009, Molecular inversion probes reveal patterns of 9p21 deletion and copy number aberrations in childhood leukemia, Cancer Genetics and Cytogenetics 193:9-18.

Schneeberger, 2011, Reference-guided assembly of four diverse *Arabidopsis thaliana* genomes, PNAS 108(25):10249-10254.

Schoolcraft, 2010, Clinical application of comprehensive chromosomal screening at the blastocyst stage, Fert Steril 94(5):1700-1706.

Schouten, 2002, Relative Quantification of 40 Nucleic Acid Sequences by Multiplex Ligation-Dependent Probe Amplification, Nucl Acids Res 30(12):257.

Schrijver, 2005, Diagnostic testing by CFTR gene mutation analysis in a large group of Hispanics, J Mol Diag 7(2):289-299.

Schuette et al., 1995, Sequence analysis of phosphorothioate oligonucleotides via matrix-assisted laser desorption ionization time-of-flight mass spectrometry, J Pharm Biomed Anal 13:1195-1203.

Schwartz et al., 2009, Identification of cystic fibrosis variants by polymerase chain reaction/oligonucleotide ligation assay, J Mol Diag 11(3):211-15.

Schwartz, 2011, Clinical utility of single nucleotide polymorphism arrays, Clin Lab Med 31(4):581-94.

Shen, 2013, Multiplex capture with double-stranded DNA probes, Genome Medicine 5(50):1-8.

Sequeira et al., 1997, Implementing generic, object-oriented models in biology, Ecological Modeling 94.1:17-31.

Sievers et al., 2011, Fast, scalable generation of high-quality protein multiple sequence alignments using Clustal Omega, Mol Syst Biol 7:539.

Simpson et al., 2009, ABySS: A parallel assembler for short read sequence data, Genome Res 19(6):1117-23.

Slater & Birney, 2005, Automated generation of heuristics for biological sequence comparison, BMC Bioinformatics 6:31.

Smirnov et al., 1996, Sequencing oligonucleotides by exonuclease digestion and delayed extraction matrix-assisted laser desorption ionization time-of-flight mass spectrometry, Anal Biochem 238:19-25.

Smith, 1985, The synthesis of oligonucleotides containing an aliphatic amino group at the 5' terminus: synthesis of fluorescent DNA primers for use in DNA sequence analysis, Nucl Acids Res 13:2399-2412.

Smith, 2010, Highly-multiplexed barcode sequencing: an efficient method for parallel analysis of pooled samples, Nucleic Acids Research 38(13):e142 (8 pages).

Soni, 2007, Progress toward ultrafast DNA sequencing using solid-state nanopores, Clin Chem 53(11):1996-2001.

Spanu et al., 2010, Genome expansion and gene loss in powdery mildew fungi reveal tradeoffs in extreme parasitism, Science 330(6010):1543-46.

Sproat, 1987, The synthesis of protected 5'-mercapto-2',5'-dideoxyribonucleoside-3'-O-phosphoramidites; uses of 5'-mercapto-oligodeoxyribonucleotides, Nucl Acids Res 15:4837-4848.

Strom, 2005, Mutation detection, interpretation, and applications in the clinical laboratory setting, Mutat Res 573:160-67.

Summerer, 2009, Enabling technologies of genomic-scale sequence enrichment for targeted high-throughput sequencing, Genomics 94(6):363-8.

Summerer, 2010, Targeted High Throughput Sequencing of a Cancer-Related Exome Subset by Specific Sequence Capture With a Fully Automated Microarray Platform, Genomics 95(4):241-246.

Sunnucks et al., 1996, Microsatellite and chromosome evolution of parthenogenetic sitobion aphids in Australia, Genetics 144:747-756.

Tan et al., 2014, "Clinical Outcome of Preimplantation Genetic Diagnosis and Screening Using Next Generation Sequencing," GigaScience 3:30, 1-9.

Thauvin-Robinet et al., 2009, The very low penetrance of cystic fibrosis for the R117H mutation: a reappraisal for genetic counseling and newborn screening, J Med Genet 46:752-758.

Thiyagarajan, 2006, PathogenMIPer: a tool for the design of molecular inversion probes to detect multiple pathogens, BMC Bioinformatics 7:500.

Thompson et al., 1994, Clustal W: improving the sensitivity of progressive multiple sequence alignment through sequence weighting, position-specific gap penalities and matrix choice, Nucl Acids Res, 22:4673-80.

Thompson et al., 2011, The properties and applications of single-molecule DNA sequencing, Genome Biology 12(2):217.

Thorstenson et al., 1998, An Automated Hydrodynamic Process for Controlled, Unbiased DNA Shearing, Genome Methods 8:848-55.

Thorvaldsdottir et al., 2012, Integrative Genomics Viewer (IGV): high-performance genomics data visualization and exploration, Briefings in Bioinformatics 24(2):178-92.

Tkachuk, 1990, Detection of bcr-abl Fusion in Chronic Myelogeneous Leukemia by in Situ Hybridization, Science 250:559.

Tobler, 2005, The SNPlex Genotyping System: A Flexible and Scalable Platform for SNP Genotyping, J Biomol Tech 16(4):398.

Tokino, 1996, Characterization of the human p57 KIP2 gene: alternative splicing, insertion/deletion polymorphisms in VNTR sequences in the coding region, and mutational analysis, Human Genetics 96:625-31.

Turner et al., 2009, Massively parallel exon capture and library-free resequencing across 16 genomes, Nature Methods 6:315-316, and Supplementary Materials (14 pages).

Turner et al., 2009, Methods for genomic partitioning, Ann Rev Hum Gen 10:263-284.

Umbarger et al., 2013, Detecting contamination in Next Generation DNA sequencinglibraries, American Society of Human Genetics 63rd Annual Meeting, Abstract, Oct. 22, 2013 (2 pages).

Umbarger, 2014, Next-generation carrier screening, Genet Med 16:132-40.

Veeneman, 2012, Oculus: faster sequence alignment by streaming read compression, BMC Bioinformatics 13:297.

Wallace & Miyada, 1987, Oligonucleotide probes for the screening of recombinant DNA libraries, Methods Enzymol 152:432-442.

Wallace et al., 1979, Hybridization of synthetic oligodeoxyribonucteotides to dp x 174DNA: the effect of single base pair mismatch, Nucleic Acids Research 6:3543-3557.

Wang et al., 2005, Allele quantification using molecular inversion probes (MIP), Nucleic Acids Research 33(21):e183.

Warner et al., 1996, A general method for the detection of large GAG repeat expansions by fluorescent PCR, J Med Genet 33(12):1022-6.

Warren et al., 2007, Assembling millions of short DNA sequences using SSAKE, Bioinformatics 23(4):500-501.

Waszak, 2010, Systematic inference of copy-number genotypes from personal genome sequencing data reveals extensive olfactory gene content diversity, PLoS Comp Biol 6(11):e1000988.

Watson et al., 2004, Cystic fibrosis population carrier screening: 2004 revision of American College of Medical Genetics mutation panel, Genetics in Medicine 6(5):387-391.

Williams, 2003, Restriction endonucleases classification, properties, and applications, Mol Biotechnol 23(3):225-43.

Wittung et al., 1997, Extended DNA-Recognition Repertoire of Peptide Nucleic Acid (PNA): PNA-dsDNA Triplex Formed with Cytosine-Rich Homopyrimidine PNA, Biochemistry 36:7973.

Wu & Aboleneen, 2001, Improved oligonucleotide sequencing by alkaline phosphatase and exonuclease digestions with mass spectrometry, Anal Biochem 290:347-352.

Wu et al., 1998, Sequencing regular and labeled oligonucleotides using enzymatic digestion and ionspray mass spectrometry, Anal Biochem 263:129-138.

Xu, 2012, FastUniq: A fast de novo duplicates removal tool for paired short reads, PLoS One 7(12):e52249.

Yau et al., 1996, Accurate diagnosis of carriers of deletions and duplications in Duchenne/Becker muscular dystrophy by fluorescent dosage analysis, Journal Medical Genetics 33(7):550-8.

Ye et al., 2009, Pindel: a pattern growth approach to detect break points of large deletions and medium sized insertions from paired-end short reads, Bioinformatics 25(21):2865-71.

Yershov, 1996, DNA analysis and diagnostics on oligonucleotide microchips, PNAS 93:4913-4918.

(56)          References Cited

OTHER PUBLICATIONS

Yoo et al., 2009, Applications of DNA Microarray in Disease Diagnostics, Journal of Microbiology and Biotechnology 19(7):635-46.

Yoon, 2014, MicroDuMIP: target-enrichment technique for microarray-based duplex molecular inversion probes, Nucl Acids Res 43(5):e28.

Yoshida et al., 2004, Role of BRCA1 and BRCA2 as regulators of DNA repair, transcription, and cell cycle in response to DNA damage, Cancer Science 95(11):866-71.

Yu, 2007, A novel set of DNA methylation markers in urine sediments for sensitive/specific detection of bladder cancer, Clin Cancer Res 13(24):7296-7304.

Yuan, 1981, Structure and mechanism of multifunctional restriction endonucleases, Ann Rev Biochem 50:285-319.

Zerbino & Birney, 2008, Velvet: algorithms for de novo short read assembly using de Bruijn graphs, Genome Res 18(5):821-829.

Zhang et al., 2011, Is Mitochondrial RNAphe Variant m.593T.Ca Synergistically Pathogenic Mutation in Chinese LHON Families with m.11778G.A? PLOS ONE 6(10):e26511.

Zhao et al., 2009, PGA4genomics for comparative genome assembly based on genetic algorithm optimization, Genomics 94(4):284-6.

Zheng et al., 2011, iAssembler: a package for de novo assembly of Roche-454/Sanger transcriptome sequences, BMC Bioinformatics 12:453.

Zhou, 2014, Bias from removing read duplication in ultra-deep sequencing experiments, Bioinformatics 30(8):1073-1080.

Zimmerman et al., 2010, A novel custom resequencing array for dilated cardiomyopathy, Genetics in Medicine 12(5):268-78.

Zuckerman, 1987, Efficient methods for attachment of thiol specific probes to the 3'-ends of synthetic oligodeoxyribonucleotides, Nucl Acids Res 15(13):5305-5321.

PCT/US13/62842, Feb. 4, 2014, International Search Report and Written Opinion.

PCT/US14/27324, Sep. 3, 2014, International Search Report and Written Opinion.

PCT/US14/28212, Dec. 9, 2014, International Search Report and Written Opinion.

PCT/US14/40516, Mar. 18, 2015, International Search Report and Written Opinion.

PCT/US14/60256, Jan. 7, 2015, International Search Report and Written Opinion.

PCT/US14/61138, Jan. 29, 2015, International Search Report and Written Opinion.

PCT/US2010/001293, Oct. 28, 2010, International Search Report and Written Opinion.

PCT/US2012/029790, Jun. 14, 2012, International Search Report and Written Opinion.

PCT/US2012/055362, Feb. 25, 2013, International Search Report and Written Opinion.

PCT/US2013/032885, Jun. 28, 2013, International Search Report and Written Opinion.

PCT/US2013/033435, Jun. 10, 2013, International Search Report and Written Opinion.

PCT/US2013/036575, Aug. 12, 2013, International Search Report and Written Opinion.

PCT/US2013/044039, Nov. 1, 2013, International Search Report and Written Opinion.

PCT/US2014/060056, Jan. 29, 2015, International Search Report and Written Opinion.

PCT/US2015/030366, Sep. 2, 2015, International Search Report and Written Opinion.

PCT/US2015/045247, Nov. 16, 2015, International Search Report and Written Opinion.

PCT/US2015/049132, Dec. 2, 2015, International Search Report and Written Opinion.

PCT/US2015/050964, Jan. 22, 2016, International Search Report and Written Opinion.

PCT/US2016/012286, May 4, 2016, International Search Report and Written Opinion.

PCT/US2016/013346, May 2, 2016, International Search Report and Written Opinion.

PCT/US2011/065098, Apr. 3, 2012, International Search Report and Written Opinion.

Alazard et al., Sequencing Oligonucleotides by Enrichment of Coupling Failures Using Matrix-Assisted Laser Desorption/Ionization Time-of-Flight Mass Spectrometry. Current Protocols in Nucleic Acid Chemistry. 2005. Chapter 10, Unit 10: 1-7.

* cited by examiner

200

205 — Obtain sequence reads from a first genomic sample and a second genomic sample amplified by FAST-SeqS 209 — Determine genotype calls at a plurality of SNP loci on the samples 213 — Generate a DNA fingerprint for each sample based on the genotype calls 217 — Compare the DNA fingerprint of the first genomic sample to the DNA fingerprint of the second genomic sample

300

305 — Obtain sequence reads from a genomic sample amplified by FAST-SeqS

309 — Identify, based on the sequence reads, a characteristic of SNPs present in the genomic sample 313 — Compare the characteristic to an expected characteristic for the genomic sample 317 — Determine, based on the comparison, whether contamination has occurred

METHODS OF QUALITY CONTROL USING SINGLE-NUCLEOTIDE POLYMORPHISMS IN PRE-IMPLANTATION GENETIC SCREENING

CROSS-REFERENCE TO RELATED APPLICATION

This application claims priority to U.S. application Ser. No. 14/995,354, filed Jan. 14, 2016, which claims the benefit of and priority to U.S. Provisional Patent Application Ser. No. 62/103,802, filed Jan. 15, 2015, the contents of each of which are incorporated herein by reference in their entirety.

FIELD OF THE INVENTION

The invention generally relates to pre-natal genetic testing, and specifically to using SNPs to validate copy number, to identify the origin of a sample, or to detect contamination in the sample.

BACKGROUND

When a woman has difficulty becoming pregnant, she may turn to in vitro fertilization (IVF). IVF involves removing one or more ova from a woman's ovary, fertilizing it and growing it in a laboratory, and implanting it into the uterus of the patient who desires to become pregnant. However, numerous difficulties with IVF exist. Successful pregnancies are only achieved in approximately 29% of cycles, and only about 22% result in live births.

One way to increase the chance of a full term pregnancy is to undergo pre-implantation genetic screening (PGS). PGS involves assessing the chromosome copy number of embryos to screen out those that are aneuploid and are thus not good candidates for implantation. Aneuploidy is a condition in which the number of chromosomes is not an exact multiple of the haploid number (23 in humans). Most aneuploidies, such as trisomy and monosomy, are lethal to the fetus. Others, such as trisomy 21 (Down syndrome), trisomy 18 (Edwards syndrome), and trisomy 13 (Patau syndrome), cause congenital defects, growth deficiencies, and intellectual disabilities in the child. PGS aims to avoid those problems by screening out aneuploid embryos from implantation.

Existing methods of PGS involve analyzing read counts of DNA sequences on each chromosome to detect differences in copy number indicative of aneuploidy. However, analytical errors can lead to false positive aneuploidy calls. Additionally, read count alone cannot distinguish certain altered copy number states, including triploidy, haploidy, and uniparental disomy.

SUMMARY

The present invention provides methods of validating the result of a pre-implantation genetic screen. Methods of the invention increase the efficacy of the PGS assay, FAST-SeqS, by taking advantage of single-nucleotide polymorphisms (SNPs) generated from the assay to confirm copy number calls, detect errors, identify samples, and recognize and identify sources of contamination. Methods of the invention increase the reliability of a PGS result, thereby making embryo selection more precise and improving outcomes of in vitro fertilization.

In embodiments, the invention provides a method for validating a putative chromosome copy number in a genomic sample using SNPs captured by FAST-SeqS method. The SNPs are sequenced to determine allele fraction across various loci. The allele fraction can be compared to the chromosome copy numbers determined by FAST-SeqS method to determine if those copy numbers are valid. For example, a copy number indicating monosomy would be invalidated by the detection of a heterozygous SNP or SNPs on a particular chromosome. Alternatively, an allele fraction showing loss of heterozygosity may prove that a copy number indicating diploidy is actually haploid. Various other permutations are described below.

In other embodiments of the invention, the SNPs amplified and sequenced in the FAST-SeqS method are utilized to generate unique DNA fingerprints, which help identify samples. DNA fingerprinting is useful for determining whether two embryos are siblings, whether two samples are from the same embryo, and whether the correct embryo was selected and implanted. It also is useful for confirming proper labeling and identification of samples during testing, thereby reducing the incidence of human error affecting IVF results.

In another embodiment, SNPs can be used to detect human contamination in a sample by calling out allele fractions or other characteristics of the SNPs that fail to conform to an expected distribution. When sample contamination has occurred, the allelic pattern of the SNPs can be used to back out the fingerprint of the contaminating sample and identify the source of contamination.

In embodiments, the SNP-based approach to calling chromosome copy numbers, DNA fingerprinting, and contamination detection can be used for other applications beyond PGS. The methods described herein are useful for cancer screening, forensics, paternity testing, screening for genetic disorders, monitoring cancer treatments, and many other uses as would be known in the art.

In certain aspects, the invention provides a method for validating a putative chromosome copy number in a genomic sample. The method involves obtaining sequencing reads from a genomic sample amplified by FAST-SeqS; enumerating read counts from the sequencing reads; calculating putative chromosome copy numbers of the genomic sample based on the read counts; obtaining allele fractions for SNPs in a region covered by the sequencing reads; and comparing the allele fractions to the putative chromosome copy numbers to validate the putative chromosome copy numbers.

In some embodiments of the method, the genomic sample is biopsied from an embryo. In some embodiments, the genomic sample comprises circulating cell-free fetal DNA, amniotic fluid, chorionic villus, fetal cells in maternal blood, trophoblasts, umbilical cord blood, tumor biopsy, or circulating tumor DNA.

In embodiments, an allele fraction that is inconsistent with the putative chromosome copy number invalidates the putative chromosome copy number. A putative chromosome copy number of 1 may indicate monosomy; a putative chromosome copy number of 2 may indicate disomy; and a putative chromosome copy number of 3 may indicate trisomy. In embodiments, an allele fraction may indicate a genomic locus is homozygous or that a genomic locus is heterozygous. An allele fraction or set of allele fractions of 100% may indicate monosomy, whereas an allele fraction or set of allele fractions of 50% may indicate disomy. An allele fraction or set of allele fractions between 10% and 40% or between 60 and 90% may indicate trisomy or tetrasomy. A putative chromosome copy number of 2 combined with allele fractions inconsistent with diploidy may indicate triploidy, haploidy, or isodisomic uniparental disomy.

In some embodiments, the method further involves identifying allele fractions that deviate from an expected allele fraction by more than a threshold amount. The threshold may be, for example, 10% or 20%. In embodiments, the method may involve diagnosing trisomy 21, trisomy 18, trisomy 13, or another aneuploidy condition.

In other aspects of the invention, a method is provided for validating a putative chromosome copy number in a genomic sample. The method involves obtaining putative chromosome copy numbers for a genomic sample, the copy numbers calculated from sequence read counts of FAST-SeqS-amplified DNA; obtaining allele fractions of SNPs in the genomic sample, the SNPs sequenced from FAST-SeqS-amplified DNA; comparing the allele fractions to the putative chromosome copy numbers; and determining whether the putative chromosome copy numbers are consistent with the allele fractions.

In certain embodiments, the genomic sample is biopsied from an embryo. The genomic sample may include circulating cell-free fetal DNA, amniotic fluid, chorionic villus, fetal cells in maternal blood, trophoblasts, umbilical cord blood, tumor biopsy, or circulating tumor DNA.

In embodiments, an allele fraction that is inconsistent with the putative chromosome copy number invalidates the putative chromosome copy number. A putative chromosome copy number of 1 may indicate monosomy; a putative chromosome copy number of 2 may indicate disomy; and a putative chromosome copy number of 3 may indicate trisomy. In embodiments, an allele fraction may indicate a genomic locus is homozygous or that a genomic locus is heterozygous. An allele fraction or set of allele fractions of 100% may indicate monosomy, whereas an allele fraction or set of allele fractions of 50% may indicate disomy. An allele fraction or set of allele fractions between 10% and 40% or between 60 and 90% may indicate trisomy or tetrasomy. A putative chromosome copy number of 2 combined with allele fractions inconsistent with diploidy may indicate triploidy, haploidy, or isodisomic uniparental disomy.

In some embodiments, the method further involves identifying allele fractions that deviate from an expected allele fraction by more than a threshold amount. The threshold may be, for example, 10% or 20%. In embodiments, the method may involve diagnosing trisomy 21, trisomy 18, trisomy 13, or another aneuploidy condition.

In other aspects, the invention provides a method for determining a degree of relatedness between two genomic samples. The method involves obtaining sequence reads from a first genomic sample and a second genomic sample amplified by FAST-SeqS; determining genotype calls at a plurality of SNP loci on the samples, based on the sequence reads; generating a DNA fingerprint for each sample based on the genotype calls; and comparing the DNA fingerprint of the first genomic sample to the DNA fingerprint of the second genomic sample to determine a degree of relatedness between the two samples. In embodiments, the first genomic sample includes a biopsy from an embryo or circulating cell-free fetal DNA.

In some embodiments of the method, generating a DNA fingerprint involves assigning a numerical score to each SNP locus and concatenating the numerical scores into a string, wherein determining a degree of relatedness involves calculating a distance metric between the DNA fingerprints. DNA fingerprinting includes numerical scores that identify at least two of the following states: heterozygous reference, heterozygous alternate, and homozygous. The method may further involve determining phylogeny based on the calculated distance metric. A degree of relatedness greater than a threshold value may indicate that the samples are identical, whereas a degree of relatedness below a threshold value may indicate the samples are from different sources. In embodiments, the first genomic sample includes DNA from an embryo and the second genomic sample is biopsied from a fetus putatively derived from the embryo. In other embodiments, the first genomic sample comprises DNA from an embryo and the second genomic sample comprises DNA from a sibling embryo.

Another aspect of the invention provides a method for detecting contamination in a sample. The method involves obtaining sequence reads from a genomic sample amplified by FAST-SeqS; identifying, based on the sequence reads, a characteristic of SNPs present in the genomic sample; comparing the characteristic to an expected characteristic for the genomic sample; and determining, based on the comparison, whether contamination has occurred.

In embodiments, the characteristic includes genotype calls, allele fractions, or a quantity of non-homozygous SNPs. The genomic sample may include a biopsy from an embryo or circulating cell-free fetal DNA. In certain embodiments of the method, the second determining step is based on whether the comparison reveals the characteristic of SNPs exceeds a threshold. The expected characteristic may be based on a characteristic of a known diploid sample.

The method may further involve determining a DNA fingerprint of a contaminant based on the comparison and identifying a source of contamination based on the DNA fingerprint.

In other aspects, the invention provides a method for determining chromosome copy number. The method involves obtaining allele fractions for SNPs sequenced by FAST-SeqS and determining chromosome copy number based on the allele fractions.

In some embodiments of the method, the genomic sample is biopsied from an embryo. In some embodiments, the genomic sample comprises circulating cell-free fetal DNA, amniotic fluid, chorionic villus, fetal cells in maternal blood, trophoblasts, umbilical cord blood, tumor biopsy, or circulating tumor DNA.

In embodiments, an allele fraction may indicate a genomic locus is homozygous or that a genomic locus is heterozygous. An allele fraction or set of allele fractions of 100% may indicate monosomy, whereas an allele fraction or set of allele fractions of 50% may indicate disomy. An allele fraction or set of allele fractions between 10% and 40% or between 60 and 90% may indicate trisomy or tetrasomy.

In some embodiments, the method further involves identifying allele fractions that deviate from an expected allele fraction by more than a threshold amount. The threshold may be, for example, 10% or 20%. In embodiments, the method may involve diagnosing trisomy 21, trisomy 18, trisomy 13, or another aneuploidy condition.

DETAILED DESCRIPTION

Figure 1:
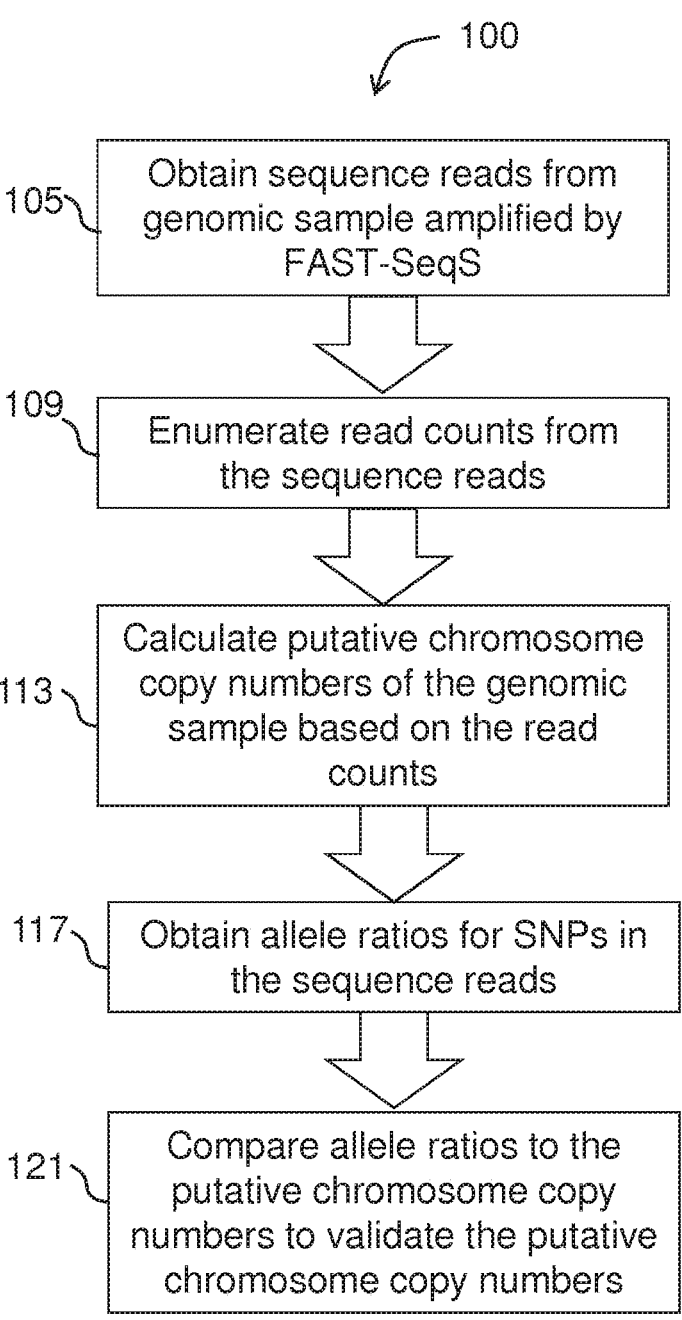
FIG. 1 shows a flowchart of a method for making copy number calls and detecting errors.

The present disclosure is generally directed to validating the results of pre-implantation genetic screening (PGS). One key objective common to PGS and multiple other genetic tests (e.g. cancer tumor sequencing and pre-natal screening) is to accurately determine the copy number of each chromosome. Such an accurate calling of chromosome copy number should enable both the identification of aneuploidy as well as the presence of an unexpected integral multiple of the haploid chromosome count. Types of aneuploidy include monosomy (one copy of a chromosome), trisomy (three copies of a chromosome), and tetrasomy (four copies of a chromosome) and common examples of unexpected integral multiples of the haploid chromosome count include triploidy (three full sets of chromosomes), tetrasomy (four full sets of chromosomes), haploidy (one set of chromosomes), and isodisomic uniparental disomy (two sets of chromosomes, both from one parent).

Methods of PGS known in the art, such as FAST-SeqS, are useful for detecting chromosomal aneuploidies and other chromosome count abnormalities. But those methods are still subject to errors (false positives and false negatives) and contamination of samples.

Single-nucleotide polymorphisms (SNPs) sequenced from an embryo grown in vitro or from circulating cell-free fetal DNA (ccffDNA) obtained from a pregnant woman, for example, can be used to provide insights about aneuploidies, other chromosome count abnormalities, and contamination. The SNPs for use with the present invention can come from DNA captured by massively parallel sequencing techniques such as FAST-SeqS.

The FAST-SeqS method involves capturing fragments from all chromosomes in a sample with a single primer pair. Using a single primer pair streamlines the PGS process. Prior techniques required preparation of whole genome libraries, which involved many complicated and technically challenging steps including, whole genome amplification, DNA fragmentation, end-repair, 5'-phosphorylation, addition of terminal dA nucleotides to 3' ends, ligation to adapters, PCR amplification, several purification steps, sequencing, and chromosome copy number calling. FAST-SeqS avoids many of those steps by using a single primer pair and a small but effective number of DNA fragments to be assessed, rather than the whole genome. See International Patent Application Publication No. WO 2013148496; and Kinde et al., 2012, "FAST-SeqS: A Simple and Efficient Method for the Detection of Aneuploidy by Massively Parallel Sequencing," PLOS ONE 7(7):e41162, the entirety of which is incorporated herein by reference.

Single-nucleotide polymorphisms (SNPs) captured and sequenced by the FAST-SeqS method can be used for a number of applications in PGS. The present disclosure provides uses for the sequenced SNPs including copy number calling and error detection, DNA fingerprinting, and detection of human contamination. As would be understood by a person of skill in the art, the SNP-based approaches described herein can be used for many other genetic screening applications beyond PGS. The methods described herein are useful for cancer screening, forensics, paternity testing, screening for genetic disorders, monitoring cancer treatments, and more.

a. Copy Number Calling and Error Detection

FAST-SeqS detects aneuploidies using chromosome copy numbers obtained from sequence reads across a chromosome of interest. However, using sequence reads alone can lead to analytical errors that yield false positive aneuploidy calls (particularly for monosomy, trisomy, and tetrasomy) and ambiguous results with respect to other chromosome count abnormalities (e.g., triploidy, haploidy, and uniparental disomy).

For example, variable sequence read depths or other analytical irregularities may contribute to a false call of monosomy when the read count data indicate that a particular chromosome has only one copy when compared with the sequence reads of other chromosomes in a sample. Using read counts alone is subject to inaccuracies. However, according to the present disclosure, a monosomy result can be confirmed by assaying SNPs of the chromosome in question.

FIG. 1 shows a method 100 for validating a putative chromosome copy number call. The method 100 includes a first step 105 of obtaining sequence reads from a genomic sample amplified by FAST-SeqS. The sample may comprise embryonic tissue, ccffDNA, chorionic villus tissue, amniotic fluid, fetal cells in maternal blood, trophoblasts, umbilical cord blood, or any other sample type known in the art for use with prenatal diagnosis. The sample may also comprise tumor DNA or circulating tumor DNA. A second step 109 comprises enumerating read counts from the sequence reads. Then in step 113 putative chromosome copy numbers are calculated based on the read counts. Optionally, a person practicing methods of the invention can begin by obtaining putative chromosome copy numbers for a genomic sample, wherein the copy numbers have been calculated from sequence read counts of FAST-SeqS-amplified DNA performed by another individual. Once putative chromosome copy numbers are obtained, the method continues in step 117 with obtaining allele fractions for SNPs captured by FAST-SeqS sequence reads.

An allele fraction is the proportion of a particular allele at a locus of interest. It may be expressed as a percentage. For example, a homozygous locus could be said to have an allele fraction of 100%, whereas a diploid locus that is heterozygous could be said to have an allele fraction of 50%. When measuring allele fraction some margin of error may be expected, and so a measured allele fraction of 47%, for example, may still be called a heterozygous diploid locus. However, as discussed in greater detail below, allele fractions that deviate significantly from 100% or 50% may be indicative of aneuploidy.

The allele fractions and the putative chromosome copy numbers are compared in step 121 to validate the putative chromosome copy numbers. Depending on what type of aneuploidy (or euploidy) is indicated by the putative chromosome copy number data, the validation step may comprise looking at different comparison metrics between the two sets of data. Generally, when an observed allele fraction is inconstant with the putative chromosome copy number, that result invalidates the putative chromosome copy number.

In one embodiment, a researcher may want to validate a monosomy call indicated by the putative chromosome copy number (i.e., copy number of 1). To detect a false monosomy call in a sample on a chromosome that is actually diploid, a researcher may look for the presence of non-homozygous genotype calls along the chromosome. An allele fraction of 100% would be consistent with monosomy, but the presence of heterozygous SNPs (presence of two alleles) at any genomic loci would reveal a copy number of at least 2. A copy number of 2 would indicate at least disomy. In such a case, the monosomy call based on read counts would prove to be an erroneous result. On the other hand, if the SNPs along the chromosome of interest revealed an apparent loss of heterozygosity, the monosomy call would be confirmed.

Using similar methods, a false trisomy or tetrasomy call can be detected as well. In a sample where read counts indicate more than two copies of a chromosome (i.e., trisomy or tetrasomy), a researcher can examine allele fractions of heterozygous SNP calls along that chromosome. In the case of a false call, heterozygous call allele fractions would not be statistically different from expectation for a diploid sample, i.e. approximately 50% for each allele. The presence of approximately 50% of each heterozygous allele would indicate that there are in fact two copies of the chromosome. A tolerance threshold can be used, wherein if an allele frequency is between, for example 45% and 55%, it is considered to be present in two copies. Alternatively, the tolerance threshold can be 40% to 60%.

However, if the allele fractions of heterozygous calls were shifted significantly from that expected for the diploid case, that would be indicative of a true trisomy or tetrasomy if observed in the presence of an elevated copy number measurement based on read count. If the allele frequencies fall outside the tolerance threshold (for example, if one allele is present at 25% and the other is present at 75%), the researcher can conclude aneuploidy exists.

Triploidy, haploidy, and isodisomic uniparental disomy present different analytical problems for the researcher. Based on read count alone, those abnormalities would appear to be diploid. That is because read count relies on the relative number of reads between chromosomes to identify outliers. Using SNPs, however, can reveal the correct ploidy level of the sample. For example, to detect triploidy (i.e., having 3 times the haploid number of chromosomes, or 3n) in a sample whose read counts yield a putative copy number of 2 for all autosomes, the sample can be assayed for the number of heterozygous SNP calls and, separately, the allele fractions of the heterozygous SNP calls in the sample. If either the number of heterozygous SNPs differs from the expectation for a diploid sample, or if the allele fraction distribution of heterozygous SNP calls differs from an expected allele fraction distribution (i.e., differs significantly from 50%), it can be inferred that the sample is triploid even though the read-based copy number measurement is indicative of diploidy.

Similarly, one can detect haploidy or isodisomic uniparental disomy (iUPD) in a sample determined to be diploid by read counts alone. The genotypes of a plurality (or preferably all) of callable known SNP loci can be assessed. If the genotypes of the plurality of SNP sites exhibits a loss of heterozygosity, one can infer the presence of haploidy or iUPD in the sample even though the read-based copy number measurement is indicative of diploidy.

Using the methods described above can confirm or refute a copy number determined by FAST-SeqS alone. The methods allow for more effective identification of chromosomal anomalies such as trisomy 21, trisomy 18, and trisomy 13.

b. DNA Fingerprinting

DNA fingerprinting (also known as DNA profiling or DNA typing) is a technique well known in the art, which can be used to identify an individual using their DNA. DNA fingerprinting relies on highly variable sequences that differ from one person to the next.

Figure 2:
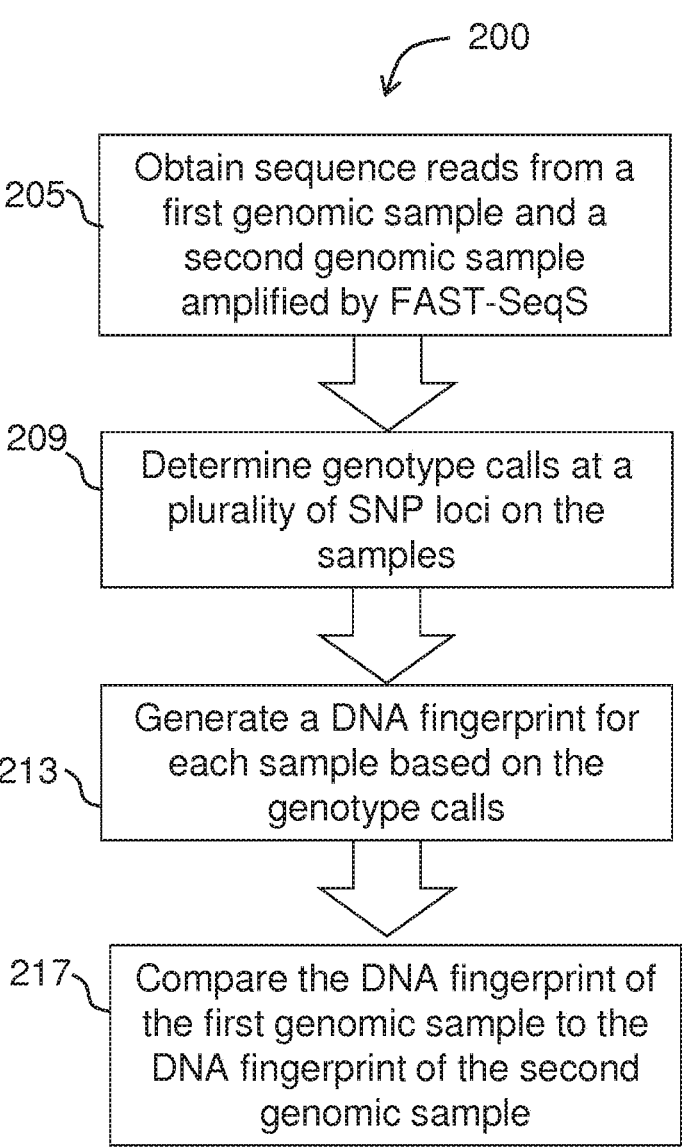
FIG. 2 shows a flowchart of a method for DNA fingerprinting.

The present disclosure provides methods of using genotype calls of SNPs from FAST-SeqS amplified DNA to generate DNA fingerprints to identify samples. The method involves performing FAST-SeqS on the sample and generating genotype calls across multiple loci. As shown in FIG. 2, a method 200 of for determining a degree of relatedness using DNA fingerprinting may comprise a first step 205 of obtaining sequence reads from two genomic samples amplified by FAST-SeqS. A sample may comprise an embryo biopsy, ccffDNA, amniotic fluid, and the like. Alternatively it could comprise saliva, blood, a buccal swab, or any other bodily cellular sample, as would be understood by those skilled in the art depending on the particular comparison to be performed. Next in step 209, genotype calls are determined at a plurality of SNP loci on the samples, based on the sequence reads. A DNA fingerprint is generated in step 213 for each sample based on the genotype calls. The genotype calls can be assigned a digital identifier or a numerical score and concatenated into a string. For example, the digital identifiers can be 0, 1, and 2, corresponding to homozygous reference, homozygous alternate, and heterozygous genotypes, respectively. Alternatively, the digital identifier could be condensed in such a manner that 0 indicates the presence of only the reference allele and 1 indicates the presence of the non-reference allele (homozygous non-reference or heterozygous).

The concatenated string of genotype calls or digital identifiers constitutes the DNA fingerprint, and can be compared to the DNA fingerprint of another sample, as shown in step 217, to determine the degree of relatedness or identity. Samples may be determined to be identical if they meet some threshold degree relatedness. Methods for determining a degree of relatedness are known in the art and may include performing clustering on the basis of a distance metric to infer relatedness.

A fingerprint assigned to a sample can serve as the basis of comparison to fingerprints from other samples to determine the degree of relatedness between them. The fingerprints can determine if two samples are unrelated, related, or identical. In the context of PGS, those fingerprints can be used to determine or rule out that a sample swap has occurred. Sample swaps can occur due to human error, either by the clinic performing the IVF or by the laboratory analyzing the biopsied tissue.

DNA fingerprinting can also be used to determine phylogenic relationships between samples, including confirming paternity. These samples can be embryo biopsies for PGS, or can be other sample types, such as ccffDNA in maternal blood, donor DNA in allograft recipients, blood or saliva samples from individuals seeking to learn about ancestry or relatedness, and biological samples for forensic applications.

In the case of determining whether a sample swap has occurred during PGS, all embryos from a given patient should exhibit a degree of relatedness equivalent to that among siblings. Any embryo from such a patient which does not exhibit a similar level of relatedness can therefore be identified as a swap. Similarly, if a sample of biological fluid or tissue is obtained from the mother, FAST-SeqS can be performed on that sample to determine the fingerprint of the mother. Using this information, it is possible to identify a gross mislabeling of all embryos from a given IVF procedure by determining their relatedness to the fingerprint derived from her sample.

In addition, it is possible to compare the FAST-SeqS fingerprint of a tested embryo before implantation to the fingerprint of a fetus, child, or product of conception supposedly derived from the embryo. That way, one could check to ensure that the chosen embryo is indeed the one that was transferred. The procedure would be done in the same manner as noted above, except rather than comparing DNA fingerprints of two embryo samples to each other, the fingerprint of an embryo would be compared to that of the alternative sample type with the expectation that the fingerprints would be identical if the correct embryo was indeed utilized.

c. Detection of Human Contamination

Human contamination in a sample being analyzed by the FAST-SeqS method can also be identified using SNPs. As would be recognized by a person skilled in the art, allele fractions for homozygous and heterozygous calls should conform to a specific expected distribution. If the distribution of allele fractions for any given sample deviates from that expectation, it can be inferred that sample contamination has occurred. It may even be possible to back out the actual fingerprint of the contaminating sample, based on the particular shift for each locus. Accordingly, one can identify the source of contamination.

Additionally, the number of heterozygous SNPs can be used to evaluate whether contamination exists. If the number of heterozygous loci is particularly large for a sample, multiple samples may have been simultaneously amplified. The number of heterozygous loci is considered large when compared to the numbers empirically observed for samples known not to be contaminated.

Figure 3:
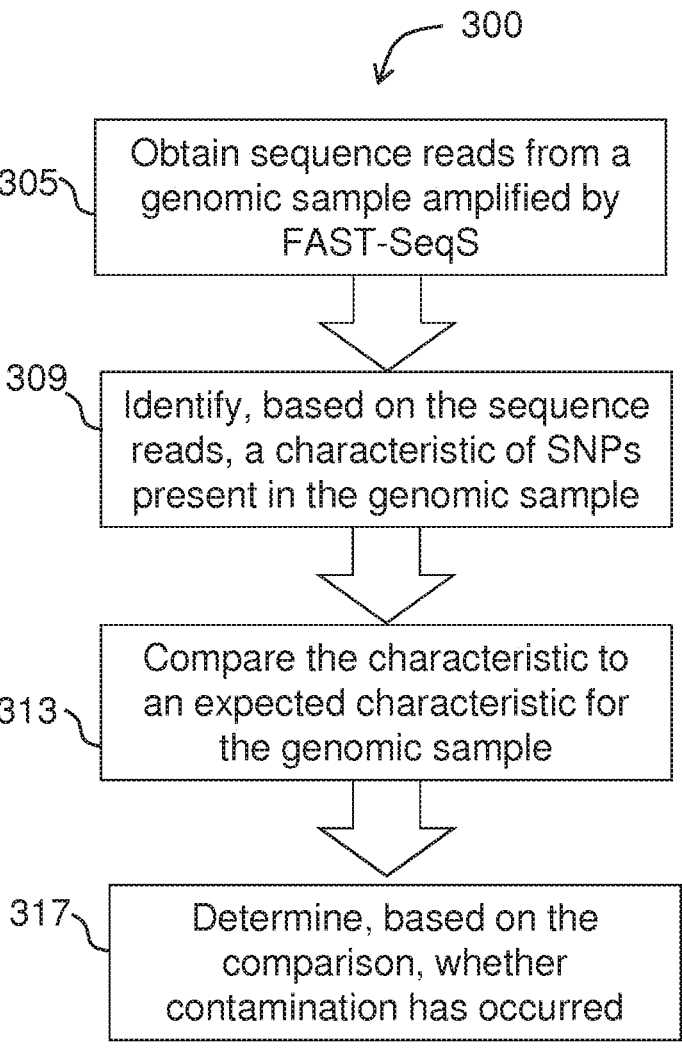
FIG. 3 shows a flowchart of a method for detecting contamination.

FIG. 3 shows a method 300 for detecting contamination in a sample in accordance with the present disclosure. The method 300 includes the first step 305 of obtaining sequence reads from a genomic sample amplified by FAST-SeqS technology. The sample may comprise embryonic tissue, ccffDNA, chorionic villus tissue, amniotic fluid, fetal cells in maternal blood, trophoblasts, umbilical cord blood, or any other sample type known in the art for use with prenatal diagnosis. The sample may also comprise tumor DNA or circulating tumor DNA. Next, in step 309, a characteristic of SNPs in the genomic sample is identified from the sequence reads. The characteristic can be genotype calls across multiple SNP loci. It can also be allele fractions at one or more SNP loci. Alternatively, the characteristic can be a quantity of non-homozygous SNPs in the sample. In some embodiments, only one of those characteristics is used. In other embodiments, multiple are used. Using multiple characteristics may increase the reliability of the result. Other similar characteristics that are known in the art can also be used.

The method 300 includes a step 313 of comparing the characteristic identified in step 309 to an expected characteristic for a non-contaminated genomic sample. For example, a practitioner of the method 300 may make a comparison to the expected genotype calls for a known diploid sample or set of diploid samples. The expected characteristic can be any of the characteristics described above that were identified in step 309. The comparison helps determine in step 313 whether the sample is an outlier and therefore contamination has occurred. That determination can be based on whether the comparison shows that the characteristic measured in the SNPs exceeds some threshold.

Optionally, if a sample is determined to be an outlier, the method 300 may comprise deducing the fingerprint of the contaminating moiety by "backing out" its genotype based on the direction of shift away from expectation for each SNP or other polymorphic locus.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A method for pre-implantation genetic screening of an embryo, the method comprising:
    obtaining a genomic sample from an embryo pre-implantation, wherein a plurality of single nucleotide polymorphisms (SNPs) are distributed throughout the genomic sample;
    performing FAST-SeqS on the genomic sample to produce sequencing reads;
    identifying, using the sequencing reads, a set of SNPs from the plurality of SNPs in a region of the genomic sample covered by the sequencing reads;
    determining, using the set of SNPs, a plurality of allele fractions for the set of SNPs in the region of the genomic sample covered by the sequencing reads, wherein each allele fraction of the plurality of allele fractions is a proportion of an allele at a particular locus within the region;
    enumerating read counts from the sequencing reads;
    determining a putative chromosome copy number of a chromosome of the genomic sample according to the read counts;
    screening out the embryo from implantation when the putative chromosome copy number indicates diploidy and the plurality of allele fractions indicate aneuploidy or unexpected integral multiples of a haploid chromosome.

2. The method of claim 1, wherein an allele fraction in the plurality of allele fractions indicates a genomic locus in the region is homozygous or heterozygous.

3. The method of claim 1, wherein a putative chromosome copy number of 2 combined with an allele fractions inconsistent with diploidy indicates triploidy, haploidy, or isodisomic uniparental disomy.

4. The method of claim 1, wherein the embryo is a human embryo.

5. The method of claim 1, further comprising implanting the embryo when the chromosome copy number and the plurality of allele fractions indicate diploidy.

6. The method of claim 1, wherein screening out the pre-implantation embryo from implantation comprises screening out when the putative chromosome copy number is diploidy and the allele fractions deviate from an expected diploid allele fraction by more than a threshold amount.

7. The method of claim 6, wherein the threshold amount is 10%.

8. The method of claim 6, wherein the threshold amount is 20%.

9. A method for confirming or refuting a putative chromosome copy number of a genomic sample of an embryo pre-implantation, the method comprising:
    obtaining a genomic sample from an embryo pre-implantation, wherein a plurality of single nucleotide polymorphisms (SNPs) are distributed throughout the genomic sample;
    performing FAST-SeqS on the genomic sample to produce sequencing reads;
    obtaining a putative chromosome copy number for the genomic sample, the putative chromosome copy number calculated from counts of the sequencing reads;

identifying, using the sequencing reads, a set of SNPs from the plurality of SNPs in a region of interest of the genomic sample covered by the sequencing reads;

determining, using the set of SNPs, a plurality of allele fractions of the set of SNPs in the region of interest in the genomic sample, wherein each allele fraction of the plurality of allele fractions is a proportion of an allele of one SNP of the set of SNPs; and confirming the putative chromosome copy number when the putative chromosome copy number is consistent with the plurality of allele fractions; or refuting the putative chromosome copy number when the putative chromosome copy number is inconsistent with the plurality of allele fractions.

10. The method of claim 9, wherein determining the putative chromosome copy number comprises determining a diploid putative chromosome copy number.

11. The method of claim 9, wherein an allele fraction of the plurality of allele fractions indicates a locus of interest is homozygous or heterozygous.

12. The method of claim 9, wherein an allele fraction of 100% and a putative chromosome copy number of 1 for the region of interest indicates monosomy; wherein an allele fraction of 50% and a putative chromosome copy number of 2 for the region of interest indicates disomy; or wherein an allele fraction between 10% and 40% or between 60% and 90% and a putative chromosome copy number of 3 for the region of interest indicates trisomy.

13. The method of claim 9, wherein a putative chromosome copy number of 2 combined with an allele fraction or allele fractions inconsistent with diploidy indicates triploidy, haploidy, or isodisomic uniparental disomy.

14. The method of claim 9, wherein the putative chromosome copy number is determined to be a trisomy 21, trisomy 18, trisomy 13, or another aneuploidy condition.

15. The method of claim 9, wherein refuting the putative chromosome copy number comprises identifying an allele fraction that deviates from an expected allele fraction of the putative chromosome copy number by more than a threshold amount.

16. The method of claim 15, wherein the threshold amount is 10%.

17. The method of claim 15, wherein the threshold amount is 20%.

18. The method of claim 9, further comprising implanting the embryo when the chromosome copy number and the plurality of allele fractions indicate diploidy.

19. The method of claim 9, wherein the embryo is a human embryo.

* * * * *